US012611450B2

(12) United States Patent
Hirano et al.

(10) Patent No.: US 12,611,450 B2
(45) Date of Patent: Apr. 28, 2026

(54) T CELL RECEPTORS AND METHODS OF USE THEREOF

(71) Applicant: University Health Network, Toronto (CA)

(72) Inventors: Naoto Hirano, Toronto (CA); Kenji Murata, Toronto (CA); Kayoko Saso, Toronto (CA)

(73) Assignee: University Health Network, Toronto (CA)

( * ) Notice: Subject to any disclaimer, the term of this patent is extended or adjusted under 35 U.S.C. 154(b) by 1116 days.

(21) Appl. No.: 17/436,943

(22) PCT Filed: Mar. 3, 2020

(86) PCT No.: PCT/IB2020/051813
§ 371 (c)(1),
(2) Date: Sep. 7, 2021

(87) PCT Pub. No.: WO2020/178744
PCT Pub. Date: Sep. 10, 2020

(65) Prior Publication Data
US 2022/0168347 A1 Jun. 2, 2022

Related U.S. Application Data

(60) Provisional application No. 62/813,651, filed on Mar. 4, 2019.

(51) Int. Cl.
| | |
|---|---|
| *A61K 39/00* | (2006.01) |
| *A61K 40/11* | (2025.01) |
| *A61K 40/32* | (2025.01) |
| *A61K 40/42* | (2025.01) |
| *C07K 14/725* | (2006.01) |
| *C07K 14/74* | (2006.01) |
| *C07K 16/28* | (2006.01) |
| *C12N 5/0783* | (2010.01) |
| *C12N 15/62* | (2006.01) |

(52) U.S. Cl.
CPC ...... *A61K 39/001192* (2018.08); *A61K 40/11* (2025.01); *A61K 40/32* (2025.01); *A61K 40/4273* (2025.01); *C07K 14/7051* (2013.01); *C07K 14/70539* (2013.01); *C07K 16/2809* (2013.01); *C07K 16/2896* (2013.01); *C12N 5/0636* (2013.01); *C12N 15/62* (2013.01); *A61K 2239/57* (2023.05); *C07K 2317/31* (2013.01); *C07K 2317/622* (2013.01); *C07K 2319/03* (2013.01); *C12N 2740/10043* (2013.01)

(58) Field of Classification Search
CPC ........... A61K 39/001192; A61K 40/11; A61K 40/32; A61K 40/4273; A61K 2239/57; A61K 48/00; A61K 31/713; A61K 38/20; A61K 45/06; A61K 2300/00; A61K 35/17; C07K 14/7051; C07K 14/70539;

C07K 16/2809; C07K 16/2896; C07K 2317/31; C07K 2317/622; C07K 2319/03; C07K 2318/20; C07K 16/30; C12N 5/0636; C12N 15/62; C12N 2740/10043; C12N 2310/14; C12N 2320/31; C12N 2330/50; C12N 2510/00; C12N 15/1138; C12N 9/22; C12N 2740/13043; G01N 33/5011; G01N 33/505; A61P 35/00
See application file for complete search history.

(56) References Cited

U.S. PATENT DOCUMENTS

| | | | |
|---|---|---|---|
| 2010/0015113 A1 | 1/2010 | Restifo et al. | |
| 2010/0112962 A1 | 5/2010 | Van Zeijl et al. | |
| 2010/0273213 A1 | 10/2010 | Mineno et al. | |
| 2012/0082692 A1 | 4/2012 | Kostas et al. | |
| 2013/0287748 A1 | 10/2013 | June et al. | |
| 2016/0317633 A1 | 11/2016 | Yee et al. | |
| 2022/0152104 A1 | 5/2022 | Hirano et al. | |

(Continued)

FOREIGN PATENT DOCUMENTS

| | | |
|---|---|---|
| CA | 2674445 A1 | 7/2008 |
| CN | 101815785 B | 6/2013 |

(Continued)

OTHER PUBLICATIONS

Huang, S., and Kamihira, M., et al., "Development of hybrid viral vectors for gene therapy," Biotechnol Adv. 31(2):208-223, Elsevier, Netherlands (Mar. 2013).
Hirano, N., et al., "Efficient presentation of naturally processed HLA class I peptides by artificial antigen-presenting cells for the generation of effective antitumor responses," Clin. Cancer Res. 12:2967-75, American Association for Cancer Research, United States (May 2006).
Butler, M., and Hirano, N., et al., "Human cell-based artificial antigen-presenting cells for cancer immunotherapy," Immunol. Rev. 257:191-209, Wiley, United States (Jan. 2014).
Eisenberg, G., et al., "Transcutaneous immunization with hydrophilic recombinant gp100 protein induces antigen-specific cellular immune response," Cell Immunol 266(1):98-103, Elsevier, Netherlands (Sep. 2010).

(Continued)

*Primary Examiner* — Julie Wu
*Assistant Examiner* — Amber K Faust
(74) *Attorney, Agent, or Firm* — Sterne, Kessler, Goldstein & Fox P.L.L.C.

(57) ABSTRACT

The present disclosure is directed recombinant T cell receptors capable of binding a gp100 epitope and nucleic acid molecules encoding the same. In some embodiments, the nucleic acid molecules further comprise a second nucleotide sequence, wherein the second nucleotide sequence or the polypeptide encoded by the second nucleotide sequence inhibits the expression of an endogenous TCR. Other aspects of the disclosure are directed to vectors comprising the nucleic acid molecule and cells comprising the recombinant TCR, the nucleic acid molecule, or the vector. Still other aspects of the disclosure are directed to methods of using the same. In some embodiments, the methods comprise treating a cancer in a subject in need thereof.

15 Claims, 8 Drawing Sheets

Specification includes a Sequence Listing.

(56)                 References Cited

U.S. PATENT DOCUMENTS

| | | |
|---|---|---|
| 2022/0152105 A1 | 5/2022 | Hirano et al. |
| 2022/0168345 A1 | 6/2022 | Hirano et al. |
| 2022/0168346 A1 | 6/2022 | Hirano et al. |
| 2022/0168347 A1 | 6/2022 | Hirano et al. |
| 2022/0169695 A1 | 6/2022 | Hirano et al. |
| 2022/0169696 A1 | 6/2022 | Hirano et al. |
| 2022/0324938 A1 | 10/2022 | Hirano et al. |

FOREIGN PATENT DOCUMENTS

| | | | |
|---|---|---|---|
| EP | 3118322 A1 | 1/2017 | |
| JP | 2012522500 A | 9/2012 | |
| JP | 2013162797 A | 8/2013 | |
| JP | 2013541332 A | 11/2013 | |
| KR | 1020180135489 A | 12/2018 | |
| WO | WO-1999045954 A1 | 9/1999 | |
| WO | WO-2001030382 A1 | 5/2001 | |
| WO | WO-0226778 A2 | 4/2002 | |
| WO | WO-2006031221 A1 * | 3/2006 | ........... A61K 48/005 |
| WO | WO-2008120202 A2 | 10/2008 | |
| WO | WO-2009051555 A2 | 4/2009 | |
| WO | WO-2010037395 A2 | 4/2010 | |
| WO | WO-2010112962 A1 | 10/2010 | |
| WO | WO-2011140284 A2 | 11/2011 | |
| WO | WO-2012038055 A1 | 3/2012 | |
| WO | WO-2014207708 A2 | 12/2014 | |
| WO | WO-2016073755 A2 | 5/2016 | |
| WO | WO-2016199140 A1 | 12/2016 | |
| WO | WO-2017120428 A2 | 7/2017 | |
| WO | WO-2017185169 A1 | 11/2017 | |
| WO | WO-2020178744 A1 | 9/2020 | |

OTHER PUBLICATIONS

Genbank, "*Homo sapiens* premelanosome protein (PMEL), transcript variant 3, mRNA," Accession No. NM_006928, accessed at https://www.ncbi.nlm.nih.gov/nuccore/NM_006928.5/ accessed on Jul. 21, 2022, 6 pages.

International Search Report and Written Opinion for International Application No. PCT/IB2020/051813, Canadian Intellectual Property Office, Quebec, mailed on Jul. 2, 2020, 12 pages.

Ikeda, H., "T-cell adoptive immunotherapy using tumor-infiltrating T cells and genetically engineered TCR-T cells," Int. Immunol. 28(7):349-353, Oxford University Press, United Kingdom (Jul. 2016).

Lowe, K.L., et al., "Novel TCR-based biologics: mobilising T cells to warm 'cold' tumours," Cancer Treat Rev. 77:35-43, Elsevier, Netherlands (Jul. 2019).

Johnson, L.A., et al., "Gene therapy with human and mouse T-ce;; receptors mediates cancer regression and targets normal tissues expressing cognate antigen," Blood 114(3):535-546, American Society of Hematology, United States (Jul. 2009).

Kagoya, Y., et al., "DOTIL inhibition attenuates graft-versus-host disease by allogeneic T cells in adoptive immunotherapy models," Nat. Commun. 9:1915, Springer Nature, Germany (May 2018).

Anczurowski, M., et al., "Mechanisms underlying the lack of endogenous processing and CLIP-mediated binding of the invariant chain by HLA-DP 84Gly," Sci. Rep. 8:4804, Springer Nature, Germany (Mar. 2018).

Yamashita, Y., et al., "HLA-DP 84Gly constitutively presents endogenous peptides generated by the class I antigen processing pathway," Nat Commun. 8:15244, Springer Nature, Germany (May 2017).

Met, O., et al., "Principles of adoptive T cell therapy in cancer," Seminars in Immunopathology 41:49-58 (Sep. 2019).

Luo, W., et al., "Anti-tuberculosis activity of TCR gene-modified T cells specific for the M. tuberculosis 38 kD antigen," Chin Sci Bull 57(18):1657-1665, Science China Press, China (Jun. 2012).

Baba, T., et al., "Phase 1 clinic trial of the vaccination fo the patients with metastatic melanoma using gp100-derived epitope peptide restricted to HLA-A*2402." Journal of Translational Medicine, 8:84, 1-12 (Sep. 2010).

Bareli R., et al., "MHC-multimer guided isolation of neoepitopes specific T cells as a potent-personalized cancer treatment strategy," OncoImmunology, vol. 5 No. 7, Feb. 23, 2016; 3 pages.

Sharma G., et al., "T-cell epitope discovery technologies," Human Immunology, vol. 75, No. 6, Apr. 19, 2014; pp. 514-519.

* cited by examiner

Transduced with

|  | A*24:02 | gp100 -intron4 |
|---|---|---|
| ☐ Malme-3M | - | + |
| ▨ Malme-3M/A*24:02 | + | + |
| ☰ SK-MEL-28 | - | + |
| ■ SK-MEL-28/A*24:02 | + | + |
| ▨ A375 | - | - |
| ▨ A375/A*24:02 | + | - |
| ⊞ A375/gp100-intron4 | - | + |
| ▨ A375/A*24:02/gp100-intron4 | + | + |

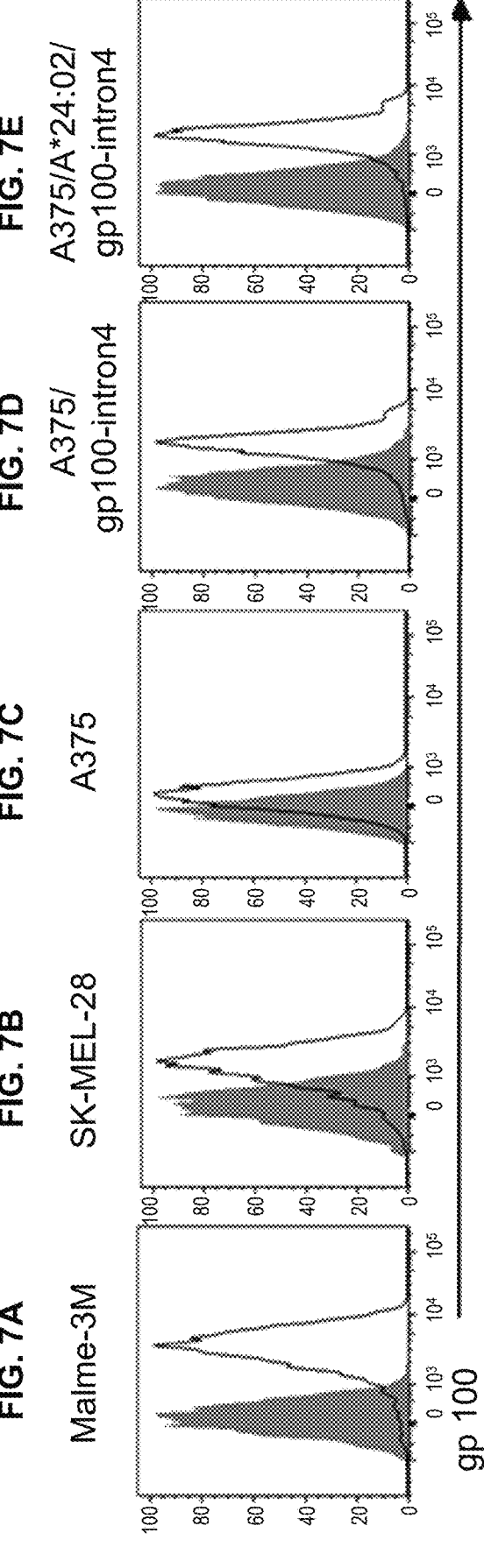

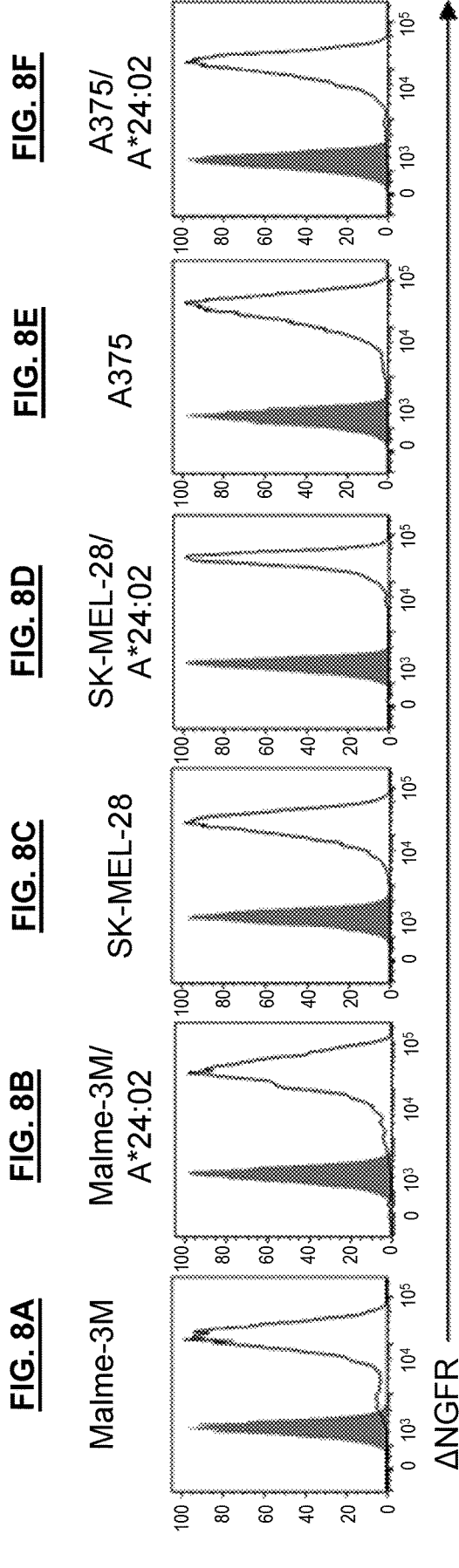

T CELL RECEPTORS AND METHODS OF USE THEREOF

CROSS REFERENCE TO RELATED APPLICATIONS

This PCT application claims the priority benefit of U.S. Provisional Application No. 62/813,651, filed Mar. 4, 2019, which is incorporated herein by reference in its entirety.

REFERENCE TO SEQUENCE LISTING SUBMITTED ELECTRONICALLY VIA EFS-WEB

The content of the electronically submitted sequence listing (Name: 4285_007PC01_Seglisting_ST25.txt, Size: 18,388 bytes; and Date of Creation: Mar. 3, 2020) is incorporated herein by reference in its entirety.

FIELD OF THE DISCLOSURE

The present disclosure provides recombinant T cell receptors ("TCRs") that specifically bind human gp100 and uses thereof.

BACKGROUND OF THE DISCLOSURE

Immunotherapy has immerged as a critical tool in the battle against a variety of diseases, including cancer. T cell therapies are at the forefront of immunotherapeutic development, and adoptive transfer of antitumor T cells has been shown induce clinical responses in cancer patients. Though many T cell therapies target mutated tumor antigens, the vast majority of neoantigens are not shared and are unique to each patient.

Potential non-mutated antigens out number mutated antigens by multiple orders of magnitude. The elucidation of T cell epitopes derived from shared antigens may facilitate the robust development of efficacious and safe adoptive T cell therapies that are readily available to a larger cohort of cancer patients. However, the sheer number of non-mutated antigens and the high polymorphism of HLA genes may have hampered comprehensive analyses of the specificity of antitumor T cell responses toward non-mutated antigens.

The present disclosure provides novel epitopes for the non-mutated antigen gp100 and TCRs capable of specifically binding the epitopes. These novel epitopes are associated with particular HLA alleles. The use of these tumor-reactive HLA-restricted gp100 TCRs stand to widen the applicability of anti-gp100 TCR gene therapy, particularly in immuno-oncology.

SUMMARY OF THE DISCLOSURE

Certain aspects of the present disclosure are directed to a nucleic acid molecule comprising (i) a first nucleotide sequence encoding a recombinant T cell receptor (TCR) or an antigen binding portion thereof that specifically binds human gp100 ("anti-gp100 TCR"); and (ii) a second nucleotide sequence, wherein the second nucleotide sequence or the polypeptide encoded by the second nucleotide sequence inhibits the expression of an endogenous TCR, wherein the anti-gp100 TCR cross competes for binding to human gp100 with a reference TCR, which comprises an alpha chain and a beta chain, and wherein the alpha chain comprises an amino acid sequence as set forth in SEQ ID NO: 1 and the beta chain comprises an amino acid sequence as set forth in SEQ ID NO: 2.

Certain aspects of the present disclosure are directed to a nucleic acid molecule comprising (i) a first nucleotide sequence encoding a recombinant T cell receptor (TCR) or an antigen binding portion thereof that specifically binds human gp100 ("anti-gp100 TCR"); and (ii) a second nucleotide sequence, wherein the second nucleotide sequence or the polypeptide encoded by the second nucleotide sequence inhibits the expression of an endogenous TCR, wherein the anti-gp100 TCR binds the same epitope or an overlapping epitope of human gp100 as a reference TCR, which comprises an alpha chain and a beta chain, wherein the alpha chain comprises an amino acid sequence as set forth in SEQ ID NO: 1 and the beta chain comprises an amino acid sequence as set forth in SEQ ID NO: 2.

In some embodiments, the anti-gp100 TCR binds to an epitope of gp100 consisting of an amino acid sequence as set forth in SEQ ID NO: 13. In some embodiments, the epitope is complexed with an HLA class I molecule.

In some embodiments, the nucleic acid molecule of claim 4, wherein the HLA class I molecule is an HLA-A, HLA-B, HLA-C, HLA-E, HLA-F, or HLA-G allele. In some embodiments, the nucleic acid molecule of claim 4, wherein the HLA class I molecule is an HLA-A*24 allele. In some embodiments, the nucleic acid molecule of any one of claims 4 to 6, wherein the HLA class I molecule is selected from an HLA-A*24:01 allele, an HLA-A*24:02 allele, and an HLA-A*24:03 allele. In some embodiments, the nucleic acid molecule of any one of claims 4 to 7, wherein the HLA class I molecule is an HLA-A*24:01 allele.

In some embodiments, the anti-gp100 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the alpha chain CDR3 comprises an amino acid sequence as set forth in SEQ ID NO: 7. In some embodiments, the beta chain CDR3 of the anti-gp100 TCR comprises an amino acid sequence as set forth in SEQ ID NO: 10.

In some embodiments, the anti-gp100 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the beta chain CDR3 of the anti-gp100 TCR comprises an amino acid sequence as set forth in SEQ ID NO: 10. In some embodiments, the alpha chain CDR3 of the anti-gp100 TCR comprises an amino acid sequence as set forth in SEQ ID NO: 7.

In some embodiments, the alpha chain CDR1 of the anti-gp100 TCR comprises an amino acid sequence as set forth in SEQ ID NO: 5. In some embodiments, the beta chain CDR1 of the anti-gp100 TCR comprises an amino acid sequence as set forth in SEQ ID NO: 8. In some embodiments, the alpha chain CDR2 of the anti-gp100 TCR comprises an amino acid sequence as set forth in SEQ ID NO: 6. In some embodiments, the beta chain CDR2 of the anti-gp100 TCR comprises an amino acid sequence as set forth in SEQ ID NO: 9.

In some embodiments, the alpha chain variable domain of the anti-gp100 TCR comprises an amino acid sequence of a variable domain present in the amino acid sequence set forth SEQ ID NO: 1. In some embodiments, the beta chain variable domain of the anti-gp100 TCR comprises an amino acid sequence of a variable domain present in the amino acid sequence set forth SEQ ID NO: 2.

In some embodiments, the alpha chain of the anti-gp100 TCR further comprises a constant region, wherein the constant region is different from endogenous constant region of the alpha chain. In some embodiments, the alpha chain of the anti-gp100 TCR further comprises a constant region, wherein the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 1. In some embodiments, the alpha chain constant region comprises an amino acid sequence comprising at least 1, at least 2, at least 3, at least 4, or at least 5 amino acid substitutions relative to a constant region present in the amino acid sequence set forth SEQ ID NO: 1. In some embodiments, the beta chain of the anti-gp100 TCR further comprises a constant region, wherein the constant region is different from endogenous constant regions of the beta chain.

In some embodiments, the beta chain of the anti-gp100 TCR further comprises a constant region, wherein the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 2. In some embodiments, the beta chain constant region comprises an amino acid sequence comprising at least 1, at least 2, at least 3, at least 4, or at least 5 amino acid substitutions relative to a constant region present in the amino acid sequence set forth SEQ ID NO: 2. In some embodiments, the alpha chain of the anti-gp100 TCR comprises an amino acid sequence as set forth in SEQ ID NO: 1.

In some embodiments, the beta chain of the anti-gp100 TCR comprises an amino acid sequence as set forth in SEQ ID NO: 2. In some embodiments, the second nucleotide sequence is one or more siRNAs that reduce the expression of endogenous TCRs.

In some embodiments, the one or more siRNAs are complementary to a target sequence within a nucleotide sequence encoding a constant region of the endogenous TCRs. In some embodiments, the one or more siRNAs comprise one or more nucleotide sequences selected from the group consisting of SEQ ID NOs: 53-56.

In some embodiments, the second nucleotide sequence encodes Cas9.

In some embodiments, the anti-gp100 TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

Certain aspects of the present disclosure are directed to a vector comprising a nucleic acid molecule disclosed herein. In some embodiments, the vector is a viral vector, a mammalian vector, or bacterial vector. In some embodiments, the vector is a retroviral vector. In some embodiments, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector. In some embodiments, the vector is a lentivirus.

Certain aspects of the present disclosure are directed to a T cell receptor (TCR) or an antigen binding portion thereof comprising an alpha chain variable domain of the anti-gp100 TCR disclosed herein and a beta chain variable domain of the anti-gp100 TCR disclosed herein. In some embodiments, the recombinant T cell receptor (TCR) or an antigen binding portion thereof that specifically binds human gp100 ("an anti-gp100 TCR"), which cross competes for binding to human gp100 with a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-gp100 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to a constant region present in the amino acid sequence set forth in SEQ ID NO: 1 or (ii) the beta chain constant region comprises an amino acid sequence having a least 1, at least 2, at least 3, at least 4, or at least 5 amino acid substitutions relative to a constant region present in the amino acid sequence of SEQ ID NO: 2.

Certain aspects of the present disclosure are directed to a recombinant T cell receptor (TCR) or an antigen binding portion thereof that specifically binds human gp100 ("an anti-gp100 TCR"), which binds the same epitope or an overlapping epitope of human gp100 as a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; an wherein the anti-gp100 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to a constant region present in the amino acid sequence set forth in SEQ ID NO: 1 or (ii) the beta chain constant region comprises an amino acid sequence having a least 1, at least 2, at least 3, at least 4, or at least 5 amino acid substitutions relative to a constant region present in the amino acid sequence set forth in SEQ ID NO: 2. In some embodiments, the anti-gp100 TCR binds to an epitope of gp100 consisting of an amino acid sequence as set forth in SEQ ID NO: 13.

In some embodiments, the epitope is complexed with an HLA class I molecule. In some embodiments, the HLA class I molecule is an HLA-A, HLA-B, HLA-C, HLA-E, HLA-F, or HLA-G allele. In some embodiments, the HLA class I molecule is an HLA-A*24 allele. In some embodiments, the HLA class I molecule is selected from an HLA-A*24:01 allele, an HLA-A*24:02 allele, and an HLA-A*24:03 allele. In some embodiments, the HLA class I molecule is an HLA-A*24:02 allele.

In some embodiments, the alpha chain of the anti-gp100 TCR comprises a variable domain comprising an alpha chain CDR1, an alpha chain CDR2, and an alpha chain CDR3; and wherein the beta chain of the anti-gp100 TCR comprises variable domain comprising a beta chain CDR1, a beta chain CDR2, and a beta chain CDR3; wherein the alpha chain CDR3 of the anti-gp100 comprises an amino acid sequence as set forth in SEQ ID NO: 7. In some embodiments, the beta chain CDR3 of the anti-gp100 TCR comprises an amino acid sequence as set forth in SEQ ID NO: 10.

In some embodiments, the alpha chain of the anti-gp100 TCR comprises a variable domain comprising an alpha chainCDR1, an alpha chain CDR2, and an alpha chain CDR3; and wherein the beta chain of the anti-gp100 TCR comprises a variable domain comprising a beta chain CDR1, a beta chain CDR2, and a beta chain CDR3; wherein the beta chain CDR3 of the anti-gp100 TCR comprises an amino acid sequence as set forth in SEQ ID NO: 10. In some embodiments, the alpha chain CDR3 of the anti-gp100 TCR comprises an amino acid sequence as set forth in SEQ ID NO: 7.

In some embodiments, the alpha chain CDR1 of the anti-gp100 TCR comprises an amino acid sequence as set forth in SEQ ID NO: 5. In some embodiments, the beta chain CDR1 of the anti-gp100 TCR comprises an amino acid sequence as set forth in SEQ ID NO: 8. In some embodiments, the alpha chain CDR2 of the anti-gp100 TCR comprises an amino acid sequence as set forth in SEQ ID NO: 6. In some embodiments, the beta chain CDR2 of the anti-gp100 TCR comprises an amino acid sequence as set forth in SEQ ID NO: 9.

In some embodiments, the alpha chain variable domain of the anti-gp100 TCR comprises an amino acid sequence of a variable domain present in the amino acid sequence set forth in SEQ ID NO: 1. In some embodiments, the beta chain variable domain of the anti-gp100 TCR comprises an amino acid sequence of a variable domain present in the amino acid sequence set forth in SEQ ID NO: 2.

In some embodiments, the alpha chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 1.

In some embodiments, the beta chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 2.

In some embodiments, the alpha chain of the anti-gp100 TCR comprises an amino acid sequence as set forth in SEQ ID NO: 1. In some embodiments, the beta chain of the anti-gp100 TCR comprises an amino acid sequence as set forth in SEQ ID NO: 2.

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein or a TCR or an antigen-binding portion thereof disclosed herein. In some embodiments, the first antigen-binding domain comprises a single chain variable fragment ("scFv"). In some embodiments, the second antigen-binding domain binds specifically to a protein expressed on the surface of a T cell. In some embodiments, the second antigen-binding domain binds specifically to CD3. In some embodiments, the second antigen-binding domain comprises an scFv. In some embodiments, the first antigen-binding domain and the second antigen-binding domain are linked or associated by a covalent bond. In some embodiments, the first antigen-binding domain and the second antigen-binding domain are linked by a peptide bond.

Certain aspects of the present disclosure are directed to a cell comprising a nucleic acid molecule disclosed herein, a vector disclosed herein, a TCR disclosed herein, a recombinant TCR disclosed herein, or a bispecific TCR disclosed herein. In some embodiments, the cell further expresses CD3. In some embodiments, the cell is selected from the group consisting of a T cell, a natural killer (NK) cell, an natural killer T (NKT) cell, or an ILC cell.

Certain aspects of the present disclosure are directed to a method of treating a cancer in a subject in need thereof, comprising administering to the subject a cell disclosed herein. In some embodiments, the cancer is selected from the group consisting of melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers.

In some embodiments, the cancer is relapsed or refractory. In some embodiments, the cancer is locally advanced. In some embodiments, the cancer is advanced. In some embodiments, the cancer is metastatic.

In some embodiments, the cells are obtained from the subject. In some embodiments, the cells are obtained from a donor other than the subject. In some embodiments, the subject is preconditioned prior to the administering of the cells. In some embodiments, the preconditioning comprises administering to the subject a chemotherapy, a cytokine, a protein, a small molecule, or any combination thereof. In some embodiments, the preconditioning comprises administering an interleukin. In some embodiments, the preconditioning comprises administering IL-2, IL-4, IL-7, IL-9, IL-15, IL-21, or any combination thereof. In some embodiments, the preconditioning comprises administering a preconditioning agent selected from the group consisting of cyclophosphamide, fludarabine, vitamin C, an AKT inhibitor, ATRA, Rapamycin, or any combination thereof. In some embodiments, the preconditioning comprises administering cyclophosphamide, fludarabine, or both.

Certain aspects of the present disclosure are directed to a method of engineering an antigen-targeting cell, comprising transducing a cell collected from a subject in need of a T cell therapy with a nucleic acid disclosed herein or a vector disclosed herein. In some embodiments, the antigen-targeting cell further expresses CD3. In some embodiments, the cell is a T cell or a natural killer (NK) cell.

Certain aspects of the present disclosure are directed to an HLA class I molecule complexed to a peptide, wherein the HLA class I molecule comprises an α1 domain, an α2 domain, an α3 domain and a β2m, and wherein the peptide consists of an amino acid sequence as set forth in SEQ ID NO: 14.

In some embodiments, the HLA class I molecule is an HLA-A, HLA-B, HLA-C, HLA-E, HLA-F, or HLA-G. In some embodiments, the HLA class I molecule is an HLA-A. In some embodiments, the HLA class I molecule is an HLA-A*24 allele. In some embodiments, the HLA class I molecule is selected from an HLA-A*24:01 allele, HLA-A*24:02 allele, and an HLA-A*24:03 allele. In some embodiments, the HLA class I molecule is an HLA-A*24:01 allele. In some embodiments, the HLA class I molecule is an HLA-A*24:02 allele.

In some embodiments, the HLA class I molecule is a monomer. In some embodiments, the HLA class I molecule is a dimer. In some embodiments, the HLA class I molecule is a trimer. In some embodiments, the HLA class I molecule is a tetramer. In some embodiments, the HLA class I molecule is a pentamer.

Certain aspects of the present disclosure are directed to an antigen presenting cell (APC), comprising an HLA class I molecule disclosed herein. In some embodiments, the HLA class I molecule is expressed on the surface of the APC.

Certain aspects of the present disclosure are directed to a method of enriching a target population of T cells obtained from a human subject, comprising contacting the T cells with an HLA class I molecule disclosed herein or an APC disclosed herein, wherein following the contacting, the enriched population of T cells comprises a higher number of T cells capable of binding the HLA class I molecule relative to the number of T cells capable of binding the HLA class I molecule prior to the contacting.

Certain aspects of the present disclosure are directed to a method of enriching a target population of T cells obtained from a human subject, comprising contacting the T cells in vitro with a peptide, wherein the peptide consists of an amino acid sequence as set forth in SEQ ID NO: 13, wherein following the contacting, the enriched population of T cells comprises a higher number of T cells capable of targeting a tumor cell relative to the number of T cells capable of targeting a tumor cell prior to the contacting.

In some embodiments, the T cells obtained from the human subject are tumor infiltrating lymphocytes (TIL).

Certain aspects of the present disclosure are directed to a method of treating a tumor in a subject in need thereof, comprising administering to the subject an enriched population of T cells disclosed herein.

Certain aspects of the present disclosure are directed to a method of enhancing cytotoxic T cell-mediated targeting of cancer cells in a subject afflicted with a cancer, comprising administering to the subject a peptide having an amino acid sequence as set forth in SEQ ID NO: 13.

Certain aspects of the present disclosure are directed to a cancer vaccine comprising a peptide having an amino acid sequence as set forth in SEQ ID NO: 13.

Certain aspects of the present disclosure are directed to a method of selecting a T cell capable of targeting a tumor cell, comprising contacting a population of isolated T cells in vitro with a peptide, wherein the peptide consists of an amino acid sequence as set forth in SEQ ID NO: 11. In some embodiments, the T cell is a tumor infiltrating lymphocytes (TIL).

BRIEF DESCRIPTION OF THE DRAWINGS

FIGS. 1A and 1C) and 14 days after stimulation (day 14; FIGS. 1B and 1D) are shown. The percentage of multimer$^+$ cells in CD8$^+$ T cells is shown.

FIGS. 3C, 3F, and 3I) and untransduced (FIGS. 3A, 3D, and 3G) were used as controls. The percentage of multimer$^+$ CD8$^+$ T cells is shown.

Figure 1:
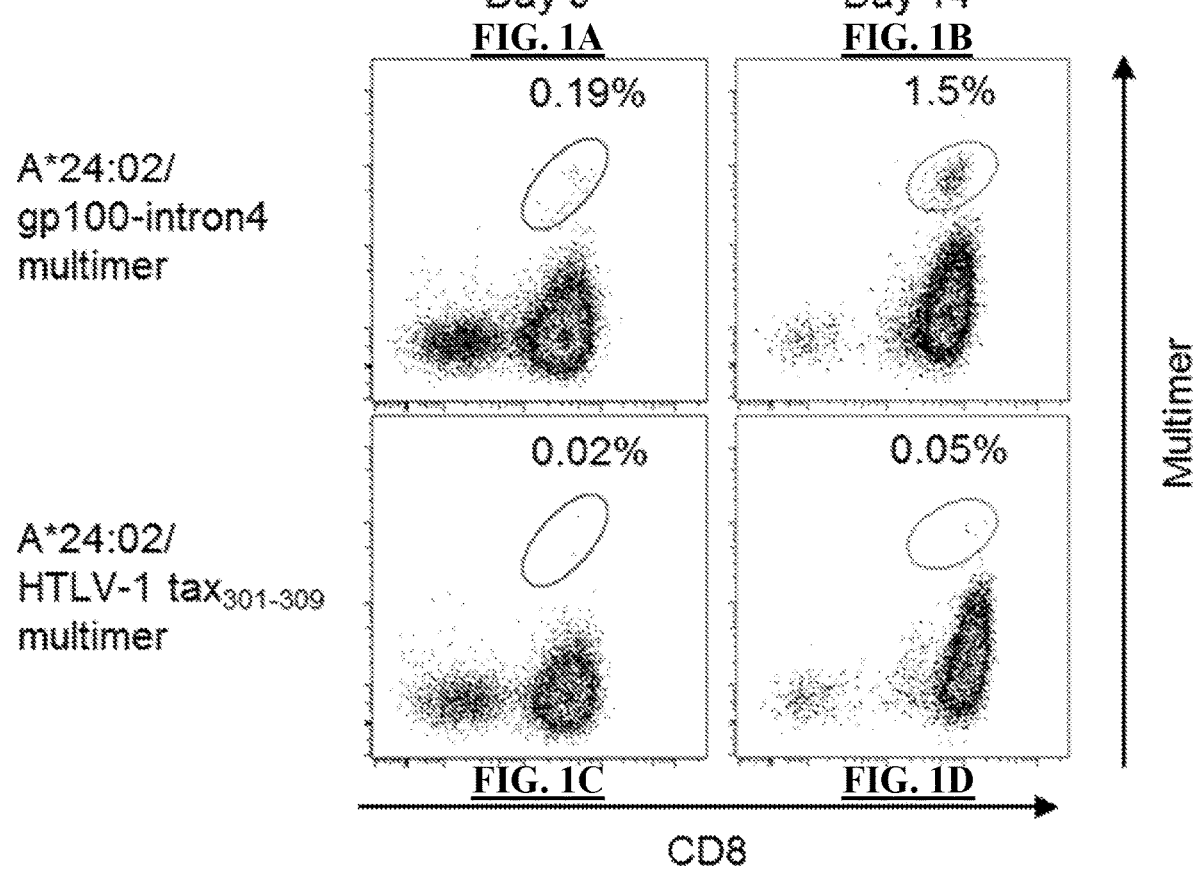
FIGS. 1A-1D are graphical representations of A*24:02/gp100-intron4 multimer staining of melanoma TILs. The TILs were stimulated once with A*24:02-artificial APCs pulsed with the gp100-intron4 peptide. Data on A*24:02/gp100-intron4 (FIGS. 1A-1B) or control A*24:02/HTLV-1 tax$_{301-309}$ multimer (FIGS. 1C-1D) staining before stimulation (day 0.

Experiments were carried out in triplicate, and error bars depict SD. *P<0.05, P<0.01, *P<0.001.

FIGS. 7A-7E are graphical representations of the expression of endogenous gp100 or transduced gp100-intron4 gene. The expression of endogenous gp100 or transduced gp100-intron4 gene in target cells was analyzed via intracellular flow cytometry following staining with anti-gp100 mAb (open curve) and an isotype control (filled curve).

FIGS. 8A-8F are graphical representations of the expression of ΔNGFR in target cells transduced with the full-length HLA-A*24:02 gene tagged with ΔNGFR (FIGS. 8B, 8D, and 8F). Surface expression of ΔNGFR in target cells transduced with the full-length HLA-A*24:02 gene tagged with ΔNGFR was analyzed by flow cytometry following staining with an anti-NGFR mAb (open curve) and an isotype control (filled curve). ΔNGFR alone was used as a control (FIGS. 8A, 8C, and 8E).

DETAILED DESCRIPTION OF THE DISCLOSURE

The present disclosure is directed to TCRs or antigen binding portions thereof that specifically bind to an epitope on gp100, nucleic acid molecules that encode the same, and cells that comprise the TCR or the nucleic acid molecule. Some aspects of the present disclosure are directed to methods of treating a caner in a subject in need thereof, comprising administering to the subject the cell. Other aspects of the present disclosure are directed to HLA class I molecules complexed to a peptide comprising the epitope of gp100.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "T cell receptor" (TCR), as used herein, refers to a heteromeric cell-surface receptor capable of specifically interacting with a target antigen. As used herein, "TCR" includes but is not limited to naturally occurring and non-naturally occurring TCRs; full-length TCRs and antigen binding portions thereof, chimeric TCRs; TCR fusion constructs; and synthetic TCRs. In human, TCRs are expressed on the surface of T cells, and they are responsible for T cell recognition and targeting of antigen presenting cells. Antigen presenting cells (APCs) display fragments of foreign proteins (antigens) complexed with the major histocompatibility complex (MHC; also referred to herein as complexed with an HLA molecule, e.g., an HLA class 1 molecule). A TCR recognizes and binds to the antigen:HLA complex and recruits CD3 (expressed by T cells), activating the TCR. The activated TCR initiates downstream signaling and an immune response, including the destruction of the EPC.

In general, a TCR can comprise two chains, an alpha chain and a beta chain (or less commonly a gamma chain and a delta chain), interconnected by disulfide bonds. Each chain comprises a variable domain (alpha chain variable domain and beta chain variable domain) and a constant region (alpha chain constant region and beta chain constant region). The variable domain is located distal to the cell membrane, and the variable domain interacts with an antigen. The constant region is located proximal to the cell membrane. A TCR can further comprises a transmembrane region and a short cytoplasmic tail. As used herein, the term "constant region" encompasses the transmembrane region and the cytoplasmic tail, when present, as well as the traditional "constant region."

The variable domains can be further subdivided into regions of hypervariability, termed complementarity determining regions (CDRs), interspersed with regions that are more conserved, termed framework regions (FR). Each alpha chain variable domain and beta chain variable domain comprises three CDRs and four FRs: FR1, CDR1, FR2, CDR2, FR3, CDR3, FR4. Each variable domain contains a binding domain that interacts with an antigen. Though all three CDRs on each chain are involved in antigen binding, CDR3 is believed to be the primary antigen binding region. CDR1 is also interacts with the antigen, while CD2 is believed to primarily recognize the HLA complex.

Where not expressly stated, and unless the context indicates otherwise, the term "TCR" also includes an antigen-binding fragment or an antigen-binding portion of any TCR disclosed herein, and includes a monovalent and a divalent fragment or portion, and a single chain TCR. The term "TCR" is not limited to naturally occurring TCRs bound to the surface of a T cell. As used herein, the term "TCR" further refers to a TCR described herein that is expressed on the surface of a cell other than a T cell (e.g., a cell that naturally expresses or that is modified to express CD3, as described herein), or a TCR described herein that is free from a cell membrane (e.g., an isolated TCR or a soluble TCR).

An "antigen binding molecule," "portion of a TCR," or "TCR fragment" refers to any portion of an TCR less than the whole. An antigen binding molecule can include the antigenic complementarity determining regions (CDRs).

An "antigen" refers to any molecule, e.g., a peptide, that provokes an immune response or is capable of being bound by a TCR. An "epitope," as used herein, refers to a portion of a polypeptide that provokes an immune response or is capable of being bound by a TCR. The immune response may involve either antibody production, or the activation of specific immunologically-competent cells, or both. A person of skill in the art would readily understand that any macromolecule, including virtually all proteins or peptides, can serve as an antigen. An antigen and/or an epitope can be endogenously expressed, i.e. expressed by genomic DNA, or can be recombinantly expressed. An antigen and/or an epitope can be specific to a certain tissue, such as a cancer cell, or it can be broadly expressed. In addition, fragments of larger molecules can act as antigens. In one embodiment, antigens are tumor antigens. An epitope can be present in a longer polypeptide (e.g., in a protein), or an epitope can be present as a fragment of a longer polypeptide. In some embodiments, an epitope is complexed with a major histocompatibility complex (MHC; also referred to herein as complexed with an HLA molecule, e.g., an HLA class 1 molecule).

"gp100," "glycoprotein 100," "melanocyte protein PMEL," or "ME20M," as used herein, refers to a tumor antigen with expression in, e.g., melanoma. gp100 is a hydrophobic glycoprotein of 661 amino acids with a molecular mass of 70 kD (GenBank Acc No._NM_006928). See, e.g., Eisenberg et al., *Cell Imunol.* 266(1):98-103 (2010). In vivo, gp100 is involved in the maturation of melanosomes from stage I to stage II. As used herein, gp100 refers to not only the full-length canonical sequence, but also variants and fragments thereof. Known variants of gp100 are provided at www.uniprot.org (UniProtKB—P40967; last accessed Mar. 1, 2019).

TABLE 1

| gp100 Amino Acid Sequence | |
| --- | --- |
| SEQ ID NO: | gp100 Amino Acid Sequence |
| 52 | MDLVLKRCLLHLAVIGALLA VGATKVPRNQDWLGVSRQLR TKAWNRQLYPEWTEAQRLDC WRGGQVSLKVSNDGPTLIGA NASFSIALNFPGSQKVLPDG QVIWVNNTIINGSQVWGGQP VYPQETDDACIFPDGGPCPS GSWSQKRSFVYVWKTWGQYW QVLGGPVSGLSIGTGRAMLG THTMEVTVYHRRGSRSYVPL AHSSSAFTITDQVPFSVSVS QLRALDGGNKHFLRNQPLTF ALQLHDPSGYLAEADLSYTW DFGDSSGTLISRALVVTHTY LEPGPVTAQVVLQAAIPLTS CGSSPVPGTTDGHRPTAEAP NTTAGQVPTTEVVGTTPGQA PTAEPSGTTSVQVPTTEVIS TAPVQMPTAESTGMTPEKVP VSEVNIGTTLAEMSTPEATG MTPAEVSIVVLSGTTAAQVT TTEWVETTARELPIPEPEGP DASSIIVISTESITGSLGPL LDGTATLRLVKRQVPLDCVL YRYGSFSVTLDIVQGIESAE ILQAVPSGEGDAFELTVSCQ GGLPKEACMEISSPGCQPPA QRLCQPVLPSPACQLVLHQI LKGGSGTYCLNVSLADTNSL AVVSTQLIMPGQEAGLGQVP LIVGILLVLMAVVLASLIYR RRLMKQDFSVPQLPHSSSHW LRLPRIFCSCPIGENSPLLS GQQV |

The term "HLA," as used herein, refers to the human leukocyte antigen. HLA genes encode the major histocompatibility complex (MHC) proteins in humans. MHC proteins are expressed on the surface of cells, and are involved in activation of the immune response. HLA class I genes encode MHC class I molecules, which are expressed on the surface of cells in complex with peptide fragments (antigens) of self or non-self proteins. T cells expressing TCR and CD3 recognize the antigen:MHC class I complex and initiate an immune response to target and destroy antigen presenting cells displaying non-self proteins.

As used herein, an "HLA class I molecule" or "HLA class I molecule" refers to a protein product of a wild-type or variant HLA class I gene encoding an MHC class I molecule. Accordingly, "HLA class I molecule" and "MHC class I molecule" are used interchangeably herein.

The MHC Class I molecule comprises two protein chains: the alpha chain and the β2-microglobulin (β2m) chain. Human β2m is encoded by the B2M gene. The amino acid sequence of β2m is set forth in SEQ ID NO: 16 (Table 2). The alpha chain of the MHC Class I molecule is encoded by the HLA gene complex. The HLA complex is located within the 6p21.3 region on the short arm of human chromosome 6 and contains more than 220 genes of diverse function. The HLA gene are highly variant, with over 20,000 HLA alleles and related alleles, including over 15,000 HLA Class I alleles, known in the art, encoding thousands of HLA proteins, including over 10,000 HLA Class I proteins (see, e.g., hla.alleles.org, last visited Feb. 27, 2019). There are at least three genes in the HLA complex that encode an MHC Class I alpha chain protein: HLA-A, HLA-B, and HLA-C. In addition, HLA-E, HLA-F, and HLA-G encode proteins that associate with the MHC Class I molecule.

TABLE 2

| Amino Acid Sequence of Human β2m | |
| --- | --- |
| SEQ ID NO: | Sequence |
| 16 | MSRSVALAVLALLSLSGLEA |
| | IQRTPKIQVYSRHPAENGKS |
| | NFLNCYVSGFHPSDIEVDLL |
| | KNGERIEKVEHSDLSFSKDW |
| | SFYLLYYTEFTPTEKDEYAC |
| | RVNHVTLSQPKIVKWDRDM |

The term "autologous" refers to any material derived from the same individual to which it is later to be re-introduced. For example, an autologous T cell therapy comprises administering to a subject a T cell that was isolated from the same subject. The term "allogeneic" refers to any material derived from one individual which is then introduced to another individual of the same species. For example, an allogeneic T cell transplantation comprises administering to a subject a T cell that was obtained from a donor other than the subject.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some embodiments, the methods of the present invention can be used to reduce the tumor size of a tumor derived from, for example, bone cancer, renal cancer, prostate cancer, breast cancer, colon cancer, lung cancer, cutaneous or intraocular malignant melanoma, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. The particular cancer can be responsive to chemo- or radiation therapy or the cancer can be refractory. A refractory cancer refers to a cancer that is not amendable to surgical intervention, and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" or "progressive disease," which can be abbreviated as PD, as used herein, refers to a worsening of one or more symptom associated with a particular disease. For example, disease progression for a subject afflicted with a cancer can include an increase in the number or size of one or more malignant lesions, tumor metastasis, and death.

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1a (MIP-1α, MIP-1a), MIP-1β (MIP-1b), gamma-induced protein 10 (IP-10), and thymus and activation regulated chemokine (TARC or CCL17).

Other examples of analytes and cytokines of the present invention include, but are not limited to chemokine (C—C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). T-cell receptors (TCR) differentiate T cells from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO–, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). A B cell makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell or a modified cell that expresses CD3, which can either be obtained from a patient or a donor. The cell can be modified to express an exogenous construct, such as, e.g., a T cell receptor (TCR) disclosed herein, which is incorporated into the cell's genome. In some embodiments, the cell is modified to express CD3.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation.

Cells used in an immunotherapy described herein can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety. An immunotherapy can also comprise administering a modified cell to a subject, wherein the modified cell expresses CD3 and a TCR disclosed herein. In some embodiments, the modified cell is not a T cell.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody.

The terms "conditioning" and "pre-conditioning" are used interchangeably herein and indicate preparing a patient in need of a T cell therapy for a suitable condition. Conditioning as used herein includes, but is not limited to, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy. In one embodiment, "conditioning" comprises increasing a serum level of one or more cytokines, e.g., interleukin 7 (IL-7), interleukin 15 (IL-15), interleukin 10 (IL-10), interleukin 5 (IL-5), gamma-induced protein 10 (IP-10), interleukin 8 (IL-8), monocyte chemotactic protein 1 (MCP-1), placental growth factor (PLGF), C-reactive protein (CRP), soluble intercellular adhesion molecule 1 (sICAM-1), soluble vascular adhesion molecule 1 (sVCAM-1), or any combination thereof. In another embodiment, "conditioning" comprises increasing a serum level of IL-7, IL-15, IP-10, MCP-1, PLGF, CRP, or any combination thereof.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Compositions of the Disclosure

The present disclosure is directed to T Cell Receptors (TCRs) or antigen binding portions thereof that specifically bind to an epitope on gp100, nucleic acid molecules that encode the same, and cells that comprise the TCR or the nucleic acid molecule. Some aspects of the present disclosure are directed to methods of treating a caner in a subject in need thereof, comprising administering to the subject a cell comprising the TCRs described herein. Other aspects of the present disclosure are directed to an epitope of gp100 that the TCRs bind to and HLA class I molecules complexed to a peptide comprising the epitope of gp100.

The T-cell receptor, or TCR, is a molecule found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The TCR is composed of two different protein chains (that is, it is a heterodimer). In humans, in 95% of T cells the TCR consists of an alpha (α) chain and a beta (β) chain (encoded by TRA and TRB, respectively), whereas in 5% of T cells, the TCR consists of gamma and delta (γ/δ) chains (encoded by TRG and TRD, respectively). This ratio changes during ontogeny and in diseased states (such as leukemia). It also differs between species. Orthologues of the 4 loci have been mapped in various species. Each locus can produce a variety of polypeptides with constant and variable regions.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors.

II.A. Nucleic Acid Molecules

Certain aspects of the present disclosure are directed to nucleic acid molecules comprising (i) a first nucleotide sequence encoding a recombinant TCR or an antigen binding portion thereof that specifically binds human gp100 ("anti-gp100 TCR"); and (ii) a second nucleotide sequence, wherein the second nucleotide sequence or the polypeptide encoded by the second nucleotide sequence inhibits the expression of an endogenous TCR. In some embodiments, the second nucleotide sequence is a non-naturally occurring sequence. In other embodiments, the second nucleotide sequence is synthetic. In yet other embodiments, the second nucleotide sequence comprises a sequence that targets a nucleotide sequence encoding the endogenous TCR. In some embodiments, the anti-gp100 TCR cross competes for binding to human gp100 with a reference TCR. In some embodiments, the anti-gp100 TCR binds the same epitope or an overlapping epitope of human gp100 as a reference TCR.

In some embodiments, the reference TCR comprises an alpha chain and a beta chain; wherein the alpha chain comprises a complementarity determining region 1 (CDR1), a CDR2, and a CDR3; wherein the beta chain comprises a CDR1, a CDR2, and a CDR3; and wherein the reference TCR comprises the alpha chain CDR3 set forth in SEQ ID NO: 7 and the beta chain CDR3 set forth in SEQ ID NO: 10. In some embodiments, the alpha chain CDR1, CDR2, and CDR3 sequences present in the an amino acid sequence set forth in SEQ ID NO: 1, and reference TCR comprises the beta chain CDR1, CDR2, and CDR3 sequences present in the amino acid sequence set forth in SEQ ID NO: 2. In some embodiments, the reference TCR comprises an alpha chain and a beta chain, wherein the alpha chain comprises an amino acid sequence as set forth in SEQ ID NO: 1 and the beta chain comprises an amino acid sequence as set forth in SEQ ID NO: 2.

TABLE 3

Alpha Chain and Beta Chain TCR Sequences

| SEQ ID NO: | TCR Chain | Sequence |
|---|---|---|
| 1 | Alpha Chain (amino acid) | METLLGLLILWLQLQWVSSK QEVTQIPAALSVPEGENLVL NCSFTDSAIYNLQWFRQDPG KGLTSLLLIQSSQREQTSGR LNASLDKSSGRSTLYIAASQ PGDSATYLCAVATDSWGKLQ FGAGTQVVVTPDIQNPDPAV YQLRDSKSSDKSVCLFTDFD SQTNVSQSKDSDVYITDKTV LDMRSMDFKSNSAVAWSNKS DFACANAFNNSIIPEDTFFP SPESSCDVKLVEKSFETDTN LNFQNLSVIGFRILLLKVAG FNLLMTLRLWSSZ |
| 17 | Alpha Chain (nucleotide) | ATGGAGACCCTCTTGGGCCT GCTTATCCTTTGGCTGCAGC TGCAATGGGTGAGCAGCAAA CAGGAGGTGACGCAGATTCC TGCAGCTCTGAGTGTCCCAG AAGGAGAAAACTTGGTTCTC AACTGCAGTTTCACTGATAG CGCTATTTACAACCTCCAGT GGTTTAGGCAGGACCCTGGG AAAGGTCTCACATCTCTGTT GCTTATTCAGTCAAGTCAGA GAGAGCAAACAAGTGGAAGA CTTAATGCCTCGCTGGATAA ATCATCAGGACGTAGTACTT TATACATTGCAGCTTCTCAG CCTGGTGACTCAGCCACCTA CCTCTGTGCTGTCGCAACTG ACAGCTGGGGGAAATTGCAG |

TABLE 3-continued

Alpha Chain and Beta Chain TCR Sequences

| SEQ ID NO: | TCR Chain | Sequence |
|---|---|---|
| | | TTTGGAGCAGGGACCCAGGT TGTGGTCACCCCAGATATCC AGAACCCTGACCCTGCCGTG TACCAGCTGAGAGACTCTAA ATCCAGTGACAAGTCTGTCT GCCTATTCACCGATTTTGAT TCTCAAACAAATGTGTCACA AAGTAAGGATTCTGATGTGT ATATCACAGACAAAACTGTG CTAGACATGAGGTCTATGGA CTTCAAGAGCAACAGTGCTG TGGCCTGGAGCAACAAATCT GACTTTGCATGTGCAAACGC CTTCAACAACAGCATTATTC CAGAAGACACCTTCTTCCCC AGCCCAGAAAGTTCCTGTGA TGTCAAGCTGGTCGAGAAAA GCTTTGAAACAGATACGAAC CTAAACTTTCAAAACCTGTC AGTGATTGGGTTCCGAATCC TCCTCCTGAAAGTGGCCGGG TTTAATCTGCTCATGACGCT GCGGCTGTGGTCCAGCTGA |
| 2 | Beta Chain (amino acid) | MLSPDLPDSAWNTRLLCHVM LCLLGAVSVAAGVIQSPRHL IKEKRETATLKCYPIPRHDT VYWYQQGPGQDPQFLISFYE KMQSDKGSIPDRFSAQQFSD YHSELNMSSLELGDSALYFC ASSLLPEGTGRVSGYTFGSG TRLTVVEDLNKVFPPEVAVF EPSEAEISHTQKATLVCLAT GFFPDHVELSWWVNGKEVHS GVSTDPQPLKEQPALNDSRY CLSSRLRVSATFWQNPRNHF RCQVQFYGLSENDEWTQDRA KPVTQIVSAEAWGRADCGFT SVSYQQGVLSATILYEILLG KATLYAVLVSALVLMAMVKR KDFZ |
| 18 | Beta Chain (nucleotide) | ATGCTTAGTCCTGACCTGCC TGACTCTGCCTGGAACACCA GGCTCCTCTGCCATGTCATG CTTTGTCTCCTGGGAGCAGT TTCAGTGGCTGCTGGAGTCA TCCAGTCCCCAAGACATCTG ATCAAAGAAAAGAGGGAAAC AGCCACTCTGAAATGCTATC CTATCCCTAGACACGACACT GTCTACTGGTACCAGCAGGG TCCAGGTCAGGACCCCCAGT TCCTCATTTCGTTTTATGAA AAGATGCAGAGCGATAAAGG AAGCATCCCTGATCGATTCT CAGCTCAACAGTTCAGTGAC TATCATTCTGAACTGAACAT GAGCTCCTTGGAGCTGGGGG ACTCAGCCCTGTACTTCTGT GCCAGCAGCCTCCTACCGGA AGGGACAGGCCGTGTAAGTG GCTACACCTTCGGTTCGGGG ACCAGGTTAACCGTTGTAGA GGACCTGAACAAGGTGTTCC CACCCGAGGTCGCTGTGTTT GAGCCATCAGAAGCAGAGAT CTCCCACACCCAAAAGGCCA CACTGGTGTGCCTGGCCACA GGCTTCTTCCCTGACCACGT GGAGCTGAGCTGGTGGGTGA ATGGGAAGGAGGTGCACAGT GGGGTCAGCACGGACCCGCA GCCCCTCAAGGAGCAGCCCG |

TABLE 3-continued

Alpha Chain and Beta Chain TCR Sequences

| SEQ ID NO: | TCR Chain | Sequence |
| --- | --- | --- |
| | | CCCTCAATGACTCCAGATAC<br>TGCCTGAGCAGCCGCCTGAG<br>GGTCTCGGCCACCTTCTGGC<br>AGAACCCCCGCAACCACTTC<br>CGCTGTCAAGTCCAGTTCTA<br>CGGGCTCTCGGAGAATGACG<br>AGTGGACCCAGGATAGGGCC<br>AAACCCGTCACCCAGATCGT<br>CAGCGCCGAGGCCTGGGGTA<br>GAGCAGACTGTGGCTTTACC<br>TCGGTGTCCTACCAGCAAGG<br>GGTCCTGTCTGCCACCATCC<br>TCTATGAGATCCTGCTAGGG<br>AAGGCCACCCTGTATGCTGT<br>GCTGGTCAGCGCCCTTGTGT<br>TGATGGCCATGGTCAAGAGA<br>AAGGATTTCTGA |

II.A.1. TCR Encoded by the First Nucleotide Sequence

The present disclosure is directed to a TCR encoded by the first nucleotide sequence described herein. In some embodiments, the anti-gp100 TCR encoded by the first nucleotide sequence comprises an alpha chain and a beta chain, wherein the alpha chain comprises a variable domain comprising an alpha chain CDR1, an alpha chain CDR2, and an alpha chain CDR3; and wherein the beta chain comprises variable domain comprising a beta chain CDR1, a beta chain CDR2, and a beta chain CDR3. In some embodiments, the anti-gp100 TCR comprises an alpha chain CDR3 comprising an amino acid sequence as set forth in SEQ ID NO: 7 (CAVATDSWGKLQF). In some embodiments, the anti-gp100 TCR comprises a beta chain CDR3 comprising an amino acid sequence as set forth in SEQ ID NO: 10 (CASSLLPEGTGRVSGYTF). In some embodiments, the non-CDR regions in the alpha chain and/or the beta chain are further modified, e.g., substitution or mutation of one amino acid, two amino acids, three amino acids, four amino acids, five amino acids, or six amino acids, thereby the alpha chain and/or the beta chain are not naturally occurring. In some embodiments, the substitutions or mutations can improve the TCRs described herein in various ways, e.g., binding affinity, binding specificity, stability, viscosity, or any combination thereof.

In some embodiments, the anti-gp100 TCR encoded by the first nucleotide sequence comprises an alpha chain CDR1, wherein the alpha chain CDR1 of the anti-gp100 TCR comprises an amino acid sequence as set forth in SEQ ID NO: 5 (DSAIYN). In some embodiments, the anti-gp100 TCR encoded by the first nucleotide sequence comprises a beta chain CDR1, wherein the beta chain CDR1 of the anti-gp100 TCR comprises an amino acid sequence as set forth in SEQ ID NO: 8 (IQSSQRE).

In some embodiments, the anti-gp100 TCR encoded by the first nucleotide sequence comprises an alpha chain CDR2, wherein the alpha chain CDR2 of the anti-gp100 TCR comprises an amino acid sequence as set forth in SEQ ID NO: 6 (PRHDT). In some embodiments, the anti-gp100 TCR encoded by the first nucleotide sequence comprises a beta chain CDR2, wherein the beta chain CDR2 of the anti-gp100 TCR comprises an amino acid sequence as set forth in SEQ ID NO: 9 (FYEKMQ).

In some embodiments, the anti-gp100 TCR encoded by the first nucleotide sequence comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some embodiments, the anti-gp100 TCR encoded by the first nucleotide sequence comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-gp100 TCR comprises an alpha chain CDR3 comprising an amino acid sequence as set forth in SEQ ID NO: 7. In some embodiments, the anti-gp100 TCR encoded by the first nucleotide sequence comprises an alpha chain variable domain present in the alpha chain amino acid sequence set forth in SEQ ID NO: 1.

In some embodiments, the anti-gp100 TCR encoded by the first nucleotide sequence comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some embodiments, the anti-gp100 TCR encoded by the first nucleotide sequence comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-gp100 TCR comprises a beta chain CDR3 comprising an amino acid sequence as set forth in SEQ ID NO: 10. In some embodiments, the anti-gp100 TCR encoded by the first nucleotide sequence comprises a beta chain variable domain present in the amino acid sequence set forth in SEQ ID NO: 2.

In some embodiments, the anti-gp100 TCR encoded by the first nucleotide further comprises an alpha chain constant region, a beta chain constant region, or both an alpha chain constant region and a beta chain constant region. In some embodiments, the anti-gp100 TCR encoded by the first nucleotide sequence comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some embodiments, the anti-gp100 TCR encoded by the first nucleotide sequence comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-gp100 TCR comprises an alpha chain CDR3 comprising an amino acid sequence as set forth in SEQ ID NO: 7. In some embodiments, the anti-gp100 TCR encoded by the first nucleotide sequence comprises an alpha chain constant region present in the alpha chain amino acid sequence set forth in SEQ ID NO: 1. In some embodiments, the anti-gp100 TCR encoded by the first nucleotide further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some embodiments, the anti-gp100 TCR encoded by the first nucleotide sequence comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some embodiments, the anti-gp100 TCR encoded by the first nucleotide sequence comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-gp100 TCR comprises a beta chain CDR3 comprising an amino acid sequence as set forth in SEQ ID NO: 10. In some embodiments, the anti-gp100 TCR encoded by the first nucleotide sequence comprises a beta chain constant region present in the amino acid sequence set forth in SEQ ID NO: 2. In some embodiments, the anti-gp100 TCR encoded by the first nucleotide further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain embodiments, the anti-gp100 TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some embodiments, the anti-gp100 TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-gp100 TCR comprises an alpha chain CDR3 comprising an amino acid sequence as set forth in SEQ ID NO: 7. In some embodiments, the anti-gp100 TCR encoded by the first nucleotide sequence comprises an alpha chain comprising the amino acid sequence set forth in SEQ ID NO: 1.

In certain embodiments, the anti-gp100 TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some embodiments, the anti-gp100 TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-gp100 TCR comprises a beta chain CDR3 comprising an amino acid sequence as set forth in SEQ ID NO: 10. In some embodiments, the anti-gp100 TCR encoded by the first nucleotide sequence comprises a beta chain comprising the amino acid sequence set forth in SEQ ID NO: 2.

In some embodiments, the anti-gp100 TCR encoded by the first nucleotide sequence comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

II.A.2. Epitopes

In some embodiments, the anti-gp100 TCR encoded by the first nucleotide sequence binds the same epitope as a reference TCR. In some embodiments, the anti-gp100 TCR binds to an epitope of gp100 comprising the amino acid sequence set forth in SEQ ID NO: 13 (VYFFLPDHL). In some embodiments, the anti-gp100 TCR binds to an epitope of gp100 consisting of an amino acid sequence as set forth in SEQ ID NO: 13. In some embodiments, the epitope consists of intron4 of gp100 (SEQ ID NO: 52), e.g., "gp100-intron4."

In certain embodiments, the epitope is complexed with an HLA class I molecule. The human leukocyte antigen (HLA) system (the major histocompatibility complex [MHC] in humans) is an important part of the immune system and is controlled by genes located on chromosome 6. It encodes cell surface molecules specialized to present antigenic peptides to the T-cell receptor (TCR) on T cells. (See also Overview of the Immune System.) MHC molecules that present antigen (Ag) are divided into 2 main classes: Class I MHC molecules and Class II MHC molecules.

Class I MHC molecules are present as transmembrane glycoproteins on the surface of all nucleated cells. Intact class I molecules consist of an alpha heavy chain bound to a beta-2 microglobulin molecule. The heavy chain consists of 2 peptide-binding domains, an Ig-like domain, and a transmembrane region with a cytoplasmic tail. The heavy chain of the class I molecule is encoded by genes at HLA-A, HLA-B, and HLA-C loci. T cells that express CD8 molecules react with class I MHC molecules. These lymphocytes often have a cytotoxic function, requiring them to be capable of recognizing any infected cell. Because every nucleated cell expresses class I MHC molecules, all infected cells can act as antigen-presenting cells for CD8 T cells (CD8 binds to the nonpolymorphic part of the class I heavy chain). Some class I MHC genes encode nonclassical MHC molecules, such as HLA-G (which may play a role in protecting the fetus from the maternal immune response) and HLA-E (which presents peptides to certain receptors on natural killer [NK] cells).

In some embodiments, the HLA class 1 molecule is selected from an HLA-A, HLA-B, and HLA-C allele. In some embodiments, the HLA class 1 molecule is selected from an HLA-E, HLA-F, and HLA-G allele. In certain embodiments, the HLA class 1 molecule is an HLA-A allele. In certain embodiments, the HLA class 1 molecule is an HLA-B allele. In certain embodiments, the HLA class 1 molecule is an HLA-C allele.

Many HLA-A, HLA-B, and HLA-C alleles are known in the art, and any of the known alleles can be used in the present disclosure. An updated list of HLA alleles is available at hla.alleles.org/ (last visited on Feb. 27, 2019). In some embodiments, the HLA class 1 molecule is an HLA-A allele selected from an HLA-A*01, an HLA-A*02, an HLA-A*03, an HLA-A*11, an HLA-A*23, an HLA-A*24, an HLA-A*25, an HLA-A*26, an HLA-A*29, an HLA- A*30, an HLA-A*31, an HLA-A*32, an HLA-A*33, an HLA-A*34, an HLA-A*36, an HLA-A*43, an HLA-A*66, an HLA-A*68, an HLA-A*69, an HLA-A*74, and an HLA-A*80. In certain embodiments, the HLA-A allele is an HLA-A*24:01 allele. In certain embodiments, the HLA-A allele is an HLA-A*24:02 allele. In certain embodiments, the HLA-A allele is an HLA-A*24:03 allele. In certain embodiments, the HLA-A allele is an HLA-A*24:11 allele. In certain embodiments, the HLA-A allele is an HLA-A*24:23 allele. In certain embodiments, the HLA-A allele is an HLA-A*24:24 allele. In certain embodiments, the HLA-A allele is an HLA-A*24:25 allele. In certain embodiments, the HLA-A allele is an HLA-A*24:26 allele.

In certain embodiments, the HLA class 1 molecule is an HLA-A allele selected from the group consisting of HLA-A*24:02:01:01, HLA-A*24:02:01:02, HLA-A*24:02:01:03, HLA-A*24:02:01:04, HLA-A*24:02:01:05, HLA-A*24:02:01:06, HLA-A*24:02:01:07, HLA-A*24:02:01:08, HLA-A*24:02:01:09, HLA-A*24:02:01:10, HLA-A*24:02:01:11, HLA-A*24:02:01:12, HLA-A*24:02:01:13, HLA-A*24:02:01:14, HLA-A*24:02:01:15, HLA-A*24:02:01:16, HLA-A*24:02:01:17, HLA-A*24:02:01:18, HLA-A*24:02:01:19, HLA-A*24:02:01:20, HLA-A*24:02:02, HLA-A*24:02:03, HLA-A*24:02:04, HLA-A*24:02:05, HLA-A*24:02:06, HLA-A*24:02:07, HLA-A*24:02:08, HLA-A*24:02:09, HLA-A*24:02:10, HLA-A*24:02:100, HLA-A*24:02:101, HLA-A*24:02:102, HLA-A*24:02:103, HLA-A*24:02:104, HLA-A*24:02:105, HLA-A*24:02:106, HLA-A*24:02:107, HLA-A*24:02:108, HLA-A*24:02:109, HLA-A*24:02:11, HLA-A*24:02:110, HLA-A*24:02:111, HLA-A*24:02:112, HLA-A*24:02:113, HLA-A*24:02:114, HLA-A*24:02:115, HLA-A*24:02:12, HLA-A*24:02:13, HLA-A*24:02:14, HLA-A*24:02:15, HLA-A*24:02:16, HLA-A*24:02:17, HLA-A*24:02:18, HLA-A*24:02:19, HLA-A*24:02:20, HLA-A*24:02:21, HLA-A*24:02:22, HLA-A*24:02:23, HLA-A*24:02:24, HLA-A*24:02:25, HLA-A*24:02:26, HLA-A*24:02:27, HLA-A*24:02:28, HLA-A*24:02:29, HLA-A*24:02:30, HLA-A*24:02:31, HLA-A*24:02:32, HLA-A*24:02:33, HLA-A*24:02:34, HLA-A*24:02:35, HLA-A*24:02:36, HLA-A*24:02:37, HLA-A*24:02:38, HLA-A*24:02:39, HLA-A*24:02:40, HLA-A*24:02:41, HLA-A*24:02:42, HLA-A*24:02:43, HLA-A*24:02:44, HLA-A*24:02:45, HLA-A*24:02:46, HLA-A*24:02:47, HLA-A*24:02:48, HLA-A*24:02:49, HLA-A*24:02:50, HLA-A*24:02:51, HLA-A*24:02:52, HLA-A*24:02:53, HLA-A*24:02:54, HLA-A*24:02:55, HLA-A*24:02:56, HLA-A*24:02:57, HLA-A*24:02:58, HLA-A*24:02:59, HLA-A*24:02:60, HLA-A*24:02:61, HLA-A*24:02:62, HLA-A*24:02:63, HLA-A*24:02:64, HLA-A*24:02:65, HLA-A*24:02:66, HLA-A*24:02:67, HLA-A*24:02:68, HLA-A*24:02:69, HLA-A*24:02:70, HLA-A*24:02:71, HLA-A*24:02:72, HLA-A*24:02:73, HLA-A*24:02:74, HLA-A*24:02:75, HLA-A*24:02:76, HLA-A*24:02:77, HLA-A*24:02:78, HLA-A*24:02:79, HLA-A*24:02:80, HLA-A*24:02:81, HLA-A*24:02:82, HLA-A*24:02:83, HLA-A*24:02:84, HLA-A*24:02:85, HLA-A*24:02:86, HLA-A*24:02:87, HLA-A*24:02:88, HLA-A*24:02:89, HLA-A*24:02:90, HLA-A*24:02:91, HLA-A*24:02:92, HLA-A*24:02:93, HLA-A*24:02:94, HLA-A*24:02:95, HLA-A*24:02:96, HLA-A*24:02:97, HLA-A*24:02:98, and HLA-A*24:02:99. In some embodiments, the HLA class 1 molecule is an HLA-A allele selected from the group consisting of HLA-A*24:03:01:01, HLA-A*24:03:01:02, HLA-A*24:03:02, HLA-A*24:03:03, HLA-A*24:03:04, HLA-A*24:04, HLA-A*24:05:01, HLA-A*24:05:02, HLA-A*24:06, HLA-A*24:07:01, HLA-A*24:07:02, HLA- A*24:08, HLA-A*24:09, HLA-A*24:100, HLA-A*24:101, HLA-A*24:102, HLA-A*24:103, HLA-A*24:104, HLA-A*24:105, HLA-A*24:106, HLA-A*24:107, HLA-A*24:108, HLA-A*24:109, HLA-A*24:10:01, HLA-A*24:10:02, HLA-A*24:110, HLA-A*24:111, HLA-A*24:112, HLA-A*24:113, HLA-A*24:114, HLA-A*24:115, HLA-A*24:116, HLA-A*24:117, HLA-A*24:118, HLA-A*24:119, HLA-A*24:11, HLA-A*24:120, HLA-A*24:121, HLA-A*24:122, HLA-A*24:123, HLA-A*24:124, HLA-A*24:125, HLA-A*24:126, HLA-A*24:127, HLA-A*24:128, HLA-A*24:129, HLA-A*24:130, HLA-A*24:131, HLA-A*24:132, HLA-A*24:133, HLA-A*24:134, HLA-A*24:135:01, HLA-A*24:135:02, HLA-A*24:136, HLA-A*24:137, HLA-A*24:138, HLA-A*24:139, HLA-A*24:13:01, HLA-A*24:13:02, HLA-A*24:140, HLA-A*24:141, HLA-A*24:142:01, HLA-A*24:142:02, HLA-A*24:143, HLA-A*24:144, HLA-A*24:145, HLA-A*24:146, HLA-A*24:147, HLA-A*24:148, HLA-A*24:149, HLA-A*24:14:01:01, HLA-A*24:14:01:02, HLA-A*24:14:01:03, HLA-A*24:15, HLA-A*24:150, HLA-A*24:151, HLA-A*24:152, HLA-A*24:153, HLA-A*24:154, HLA-A*24:155, HLA-A*24:156, HLA-A*24:157, HLA-A*24:158, HLA-A*24:159, HLA-A*24:160, HLA-A*24:161, HLA-A*24:162, HLA-A*24:163, HLA-A*24:164, HLA-A*24:165, HLA-A*24:166, HLA-A*24:167, HLA-A*24:168, HLA-A*24:169, HLA-A*24:17, HLA-A*24:170, HLA-A*24:171, HLA-A*24:172:01, HLA-A*24:172:02, HLA-A*24:173, HLA-A*24:174, HLA-A*24:175, HLA-A*24:176, HLA-A*24:177, HLA-A*24:178, HLA-A*24:179, HLA-A*24:18, HLA-A*24:180, HLA-A*24:181, HLA-A*24:182, HLA-A*24:183, HLA-A*24:184, HLA-A*24:185, HLA-A*24:186, HLA-A*24:187, HLA-A*24:188, HLA-A*24:189, HLA-A*24:19, HLA-A*24:190, HLA-A*24:191, HLA-A*24:192, HLA-A*24:193, HLA-A*24:194, HLA-A*24:195, HLA-A*24:196, HLA-A*24:197, HLA-A*24:198, HLA-A*24:199, HLA-A*24:200, HLA-A*24:201, HLA-A*24:202, HLA-A*24:203, HLA-A*24:204, HLA-A*24:205, HLA-A*24:206, HLA-A*24:207:01, HLA-A*24:207:02, HLA-A*24:208:01, HLA-A*24:208:02, HLA-A*24:209, HLA-A*24:20:01:01, HLA-A*24:20:01:02, HLA-A*24:210, HLA-A*24:212, HLA-A*24:213, HLA-A*24:214, HLA-A*24:215, HLA-A*24:216, HLA-A*24:217, HLA-A*24:218, HLA-A*24:219, HLA-A*24:21:01, HLA-A*24:21:02, HLA-A*24:21:03, HLA-A*24:22, HLA-A*24:220, HLA-A*24:221, HLA-A*24:222, HLA-A*24:223, HLA-A*24:224, HLA-A*24:225:01, HLA-A*24:225:02, HLA-A*24:226:01, HLA-A*24:226:02, HLA-A*24:227, HLA-A*24:228, HLA-A*24:229, HLA-A*24:23, HLA-A*24:230, HLA-A*24:231, HLA-A*24:232, HLA-A*24:233, HLA-A*24:234, HLA-A*24:235, HLA-A*24:236, HLA-A*24:237, HLA-A*24:238, HLA-A*24:239, HLA-A*24:24, HLA-A*24:240, HLA-A*24:241, HLA-A*24:242, HLA-A*24:243, HLA-A*24:244, HLA-A*24:245, HLA-A*24:246, HLA-A*24:247, HLA-A*24:248, HLA-A*24:249, HLA-A*24:25, HLA-A*24:250, HLA-A*24:251, HLA-A*24:252, HLA-A*24:253, HLA-A*24:254, HLA-A*24:255, HLA-A*24:256, HLA-A*24:257, HLA-A*24:258, HLA-A*24:259, HLA-A*24:26, HLA-A*24:260, HLA-A*24:261, HLA-A*24:262, HLA-A*24:263, HLA-A*24:264, HLA-A*24:265, HLA-A*24:266, HLA-A*24:267, HLA-A*24:268, HLA-A*24:269, HLA-A*24:27, HLA-A*24:270, HLA-A*24:271, HLA-A*24:272, HLA-A*24:273, HLA-A*24:274, HLA-A*24:275, HLA-A*24:276, HLA-A*24:277, HLA-A*24:278, HLA-A*24:279, HLA-A*24:28, HLA-A*24:280, HLA-A*24:281, HLA-A*24:282, HLA-A*24:283, HLA-A*24:284, HLA-A*24:285, HLA-A*24:286, HLA- A*24:287, HLA-A*24:288, HLA-A*24:289, HLA-A*24:29, HLA-A*24:290, HLA-A*24:291, HLA-A*24:292, HLA-A*24:293, HLA-A*24:294, HLA-A*24:295, HLA-A*24:296, HLA-A*24:297, HLA-A*24:298, HLA-A*24:299, HLA-A*24:30, HLA-A*24:300, HLA-A*24:301, HLA-A*24:302, HLA-A*24:303, HLA-A*24:304, HLA-A*24:305, HLA-A*24:306, HLA-A*24:307, HLA-A*24:308, HLA-A*24:309, HLA-A*24:31, HLA-A*24:310:01, HLA-A*24:310:02, HLA-A*24:311, HLA-A*24:312, HLA-A*24:313:01, HLA-A*24:313:02, HLA-A*24:314, HLA-A*24:315, HLA-A*24:316, HLA-A*24:317, HLA-A*24:318, HLA-A*24:319, HLA-A*24:32, HLA-A*24:320, HLA-A*24:321, HLA-A*24:322, HLA-A*24:323, HLA-A*24:324, HLA-A*24:325, HLA-A*24:326, HLA-A*24:327, HLA-A*24:328, HLA-A*24:329, HLA-A*24:33, HLA-A*24:330, HLA-A*24:331, HLA-A*24:332, HLA-A*24:333, HLA-A*24:334, HLA-A*24:335, HLA-A*24:336, HLA-A*24:337, HLA-A*24:338, HLA-A*24:339, HLA-A*24:34, HLA-A*24:340, HLA-A*24:341, HLA-A*24:342, HLA-A*24:343, HLA-A*24:344, HLA-A*24:345, HLA-A*24:346, HLA-A*24:347:01, HLA-A*24:347:02, HLA-A*24:348, HLA-A*24:349, HLA-A*24:35, HLA-A*24:350, HLA-A*24:351, HLA-A*24:352, HLA-A*24:353, HLA-A*24:354, HLA-A*24:355, HLA-A*24:356, HLA-A*24:357, HLA-A*24:358, HLA-A*24:359, HLA-A*24:360, HLA-A*24:361, HLA-A*24:362, HLA-A*24:363, HLA-A*24:364, HLA-A*24:365, HLA-A*24:366, HLA-A*24:367, HLA-A*24:368, HLA-A*24:369, HLA-A*24:36, HLA-A*24:37, HLA-A*24:370, HLA-A*24:371, HLA-A*24:372, HLA-A*24:373, HLA-A*24:374, HLA-A*24:375, HLA-A*24:376, HLA-A*24:377, HLA-A*24:378, HLA-A*24:379, HLA-A*24:38, HLA-A*24:380, HLA-A*24:381, HLA-A*24:382, HLA-A*24:383, HLA-A*24:384, HLA-A*24:385, HLA-A*24:386, HLA-A*24:387, HLA-A*24:388, HLA-A*24:389, HLA-A*24:39, HLA-A*24:390, HLA-A*24:391, HLA-A*24:392, HLA-A*24:393, HLA-A*24:394, HLA-A*24:395, HLA-A*24:396, HLA-A*24:397, HLA-A*24:398, HLA-A*24:399, HLA-A*24:400, HLA-A*24:401, HLA-A*24:402, HLA-A*24:403, HLA-A*24:404, HLA-A*24:405, HLA-A*24:406, HLA-A*24:407, HLA-A*24:408, HLA-A*24:409, HLA-A*24:40, HLA-A*24:41, HLA-A*24:410, HLA-A*24:411, HLA-A*24:412, HLA-A*24:413, HLA-A*24:414, HLA-A*24:415, HLA-A*24:416, HLA-A*24:417, HLA-A*24:418, HLA-A*24:419, HLA-A*24:42, HLA-A*24:420, HLA-A*24:421, HLA-A*24:422, HLA-A*24:423, HLA-A*24:424, HLA-A*24:425, HLA-A*24:426, HLA-A*24:427, HLA-A*24:428, HLA-A*24:429, HLA-A*24:43, HLA-A*24:430, HLA-A*24:431, HLA-A*24:432, HLA-A*24:433, HLA-A*24:44, HLA-A*24:45, HLA-A*24:46, HLA-A*24:47, HLA-A*24:48, HLA-A*24:49, HLA-A*24:50, HLA-A*24:51, HLA-A*24:52, HLA-A*24:53, HLA-A*24:54, HLA-A*24:55, HLA-A*24:56, HLA-A*24:57, HLA-A*24:58, HLA-A*24:59, HLA-A*24:60, HLA-A*24:61, HLA-A*24:62, HLA-A*24:63, HLA-A*24:64, HLA-A*24:66, HLA-A*24:67, HLA-A*24:68, HLA-A*24:69, HLA-A*24:70, HLA-A*24:71, HLA-A*24:72, HLA-A*24:73, HLA-A*24:74:01, HLA-A*24:74:02, HLA-A*24:75, HLA-A*24:76, HLA-A*24:77, HLA-A*24:78, HLA-A*24:79, HLA-A*24:80, HLA-A*24:81, HLA-A*24:82, HLA-A*24:83, HLA-A*24:84, HLA-A*24:85, HLA-A*24:86, HLA-A*24:87, HLA-A*24:88, HLA-A*24:89, HLA-A*24:90:01, HLA-A*24:90:02, HLA-A*24:91, HLA-A*24:92, HLA-A*24:93, HLA-A*24:94, HLA-A*24:95, HLA-A*24:96, HLA-A*24:97, HLA-A*24:98, and HLA-A*24:99.

II.A.3 The Second Nucleotide Sequence

The second nucleotide sequence of the nucleic acid molecule disclosed herein can be any sequence or can encode for any polypeptide that is capable of inhibiting the expression of an endogenous TCR. In some embodiments, the second nucleotide sequence is one or more siRNAs. In some embodiments, the one or more siRNAs are complementary to a target sequence within a nucleotide sequence encoding a constant region of an endogenous TCR. In certain embodiments, the one or more siRNAs are complementary to a target sequence within a nucleotide sequence encoding a constant region of wild-type, human TCR. In some embodiments, the one or more siRNAs are complementary to a target sequence within a nucleotide sequence encoding a constant region of the alpha chain of wild-type TCR. In some embodiments, the one or more siRNAs are complementary to a target sequence within a nucleotide sequence encoding a constant region of the beta chain of wild-type TCR. In some embodiments, the one or more siRNAs comprise (i) one or more siRNA's that are complementary to a target sequence within a nucleotide sequence encoding a constant region of the alpha chain of wild-type TCR and (ii) one or more siRNA's that are complementary to a target sequence within a nucleotide sequence encoding a constant region of the beta chain of wild-type TCR.

In some embodiments, the one or more siRNAs comprise a nucleotide sequence selected from the group consisting of SEQ ID NOs: 53-56 (Table 4). In some embodiments, the second nucleotide sequence of the nucleic acid molecule encodes one or more siRNAs, wherein the one or more siRNAs are complementary to a target sequence within a nucleotide sequence encoding a constant region of the alpha chain of wild-type TCR, and wherein the one or more siRNAs comprise the nucleic acid sequences set forth in SEQ ID NOs: 53 and 54.

TABLE 4 siRNA Sequences

| SEQ ID NO: | siRNA | Sequence (Nucleotides 1-19 are ribonucleotides; nucleotides 20-21 are deoxyribonucleotides) |
|---|---|---|
| 53 | siRNA-TCRa-1 | GUAAGGAUUCUGAUGUGUAUU |
| 54 | siRNA-TCRa-2 | UACACAUCAGAAUCCUUACUU |
| 55 | siRNA-TCRb-1 | CCACCAUCCUCUAUGAGAUUU |
| 56 | siRNA-TCRb-2 | AUCUCAUAGAGGAUGGUGGUU |

In some embodiments, the second nucleotide sequence of the nucleic acid molecule encodes one or more siRNAs, wherein the one or more siRNAs are complementary to a target sequence within a nucleotide sequence encoding a constant region of the beta chain of wild-type TCR, and wherein the one or more siRNAs comprise the nucleic acid sequences set forth in SEQ ID NOs: 55 and 56. In some embodiments, the second nucleotide sequence of the nucleic acid molecule encodes one or more siRNAs, wherein the one or more siRNAs comprise (i) one or more siRNAs that are complementary to a target sequence within a nucleotide sequence encoding a constant region of the alpha chain of wild-type TCR, wherein the one or more siRNAs comprise the nucleic acid sequences set forth in SEQ ID NOs: 53 and 54; and (ii) one or more siRNAs that are complementary to a target sequence within a nucleotide sequence encoding a constant region of the beta chain of wild-type TCR, wherein the one or more siRNAs comprise the nucleic acid sequences set forth in SEQ ID NOs: 55 and 56.

In some embodiments, the second nucleotide sequence of the nucleic acid molecule comprises SEQ ID NOs: 53-56. In some embodiments, the second nucleotide sequence comprises SEQ ID NOs: 53-56, wherein one or more of SEQ ID NOs: 53-56 is separated by one or more nucleic acids that do not encode an siRNA. In certain embodiments, the one or more siRNAs are selected from the siRNAs disclosed in U.S. Publication No. 2010/0273213 A1, which is incorporated by reference herein in its entirety.

In some embodiments, the second nucleotide sequence of the nucleic acid molecule encodes a protein, wherein the protein is capable of inhibiting the expression of an endogenous, e.g., wild-type, TCR. In some embodiments, the second nucleotide sequence encodes Cas9.

II.A.3 Vectors

Certain aspects of the present disclosure are directed to vectors comprising a nucleic acid molecule disclosed herein. In some embodiments, the vector is a viral vector. In some embodiments, the vector is a viral particle or a virus. In some embodiments, the vector is a mammalian vector. In some embodiments, the vector is a bacterial vector.

In certain embodiments, the vector is a retroviral vector. In some embodiments, the vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular embodiments, the vector is an AAV vector. In some embodiments, the vector is a lentivirus. In particular embodiments, the vector is an AAV vector. In some embodiments, the vector is a Sendai virus. In some embodiments, the vector is a hybrid vector. Examples of hybrid vectors that can be used in the present disclosure can be found in Huang and Kamihira, *Biotechnol. Adv.* 31(2):208-23 (2103), which is incorporated by reference herein in its entirety.

II.B. Recombinant T Cell Receptors (TCRs)

Certain aspects of the present disclosure are directed to recombinant T cell receptors (TCRs) or an antigen binding portion thereof that specifically bind human gp100 ("an anti-gp100 TCR"). In some embodiments, the anti-gp100 TCR is encoded by the a nucleic acid molecule disclosed herein.

In some embodiments, the anti-gp100 TCR cross competes for binding to human gp100 with a reference TCR. In some embodiments, the anti-gp100 TCR binds the same epitope or an overlapping epitope of human gp100 as a reference TCR. In some embodiments, the reference TCR comprises an alpha chain and a beta chain, and the alpha chain comprises of the reference TCR comprises an amino acid sequence as set forth in SEQ ID NO: 1. In some embodiments, the beta chain of the reference TCR comprises an amino acid sequence as set forth in SEQ ID NO: 2.

In some embodiments, the anti-gp100 TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1. In some embodiments, the anti-gp100 TCR comprises an alpha chain and a beta chain, wherein the alpha chain comprises a constant region, and wherein the beta chain comprises a constant region; wherein the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some embodiments, the anti-gp100 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some embodiments, the alpha chain of the anti-gp100 TCR comprises a variable domain comprising an alpha chain CDR1, an alpha chain CDR2, and an alpha chain CDR3; and the beta chain of the anti-gp100 TCR comprises a variable domain comprising a beta chain CDR1, a beta chain CDR2, and a beta chain CDR3. In some embodiments, the anti-gp100 TCR comprises an alpha chain CDR3 comprising an amino acid sequence as set forth in SEQ ID NO: 7. In some embodiments, the anti-gp100 TCR comprises a beta chain CDR3 comprising an amino acid sequence as set forth in SEQ ID NO: 10.

In some embodiments, the alpha chain CDR1 of the anti-gp100 TCR comprises an amino acid sequence as set forth in SEQ ID NO: 5. In some embodiments, the beta chain CDR1 of the anti-gp100 TCR comprises an amino acid sequence as set forth in SEQ ID NO: 8.

In some embodiments, the alpha chain CDR2 of the anti-gp100 TCR comprises an amino acid sequence as set forth in SEQ ID NO: 6. In some embodiments, the beta chain CDR2 of the anti-gp100 TCR comprises an amino acid sequence as set forth in SEQ ID NO: 9.

In some embodiments, the anti-gp100 TCR comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some embodiments, the anti-gp100 TCR comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-gp100 TCR comprises an alpha chain CDR3 comprising an amino acid sequence as set forth in SEQ ID NO: 7. In some embodiments, the anti-gp100 TCR comprises an alpha chain variable domain present in the alpha chain amino acid sequence set forth in SEQ ID NO: 1.

In some embodiments, the anti-gp100 TCR comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some embodiments, the anti-gp100 TCR comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-gp100 TCR comprises a beta chain CDR3 comprising an amino acid sequence as set forth in SEQ ID NO: 10. In some embodiments, the anti-gp100 TCR comprises a beta chain variable domain present in the beta chain amino acid sequence set forth in SEQ ID NO: 2.

In some embodiments, the anti-gp100 TCR encoded by the first nucleotide further comprises an alpha chain constant region, a beta chain constant region, or both an alpha chain constant region and a beta chain constant region. In some embodiments, the anti-gp100 TCR comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some embodiments, the anti-gp100 TCR comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-gp100 TCR comprises an alpha chain CDR3 comprising an amino acid sequence as set forth in SEQ ID NO: 7. In some embodiments, the anti-gp100 TCR comprises an alpha chain constant region present in the alpha chain amino acid sequence set forth in SEQ ID NO: 1. In some embodiments, the anti-gp100 TCR encoded by the first nucleotide further comprises an alpha constant region that is different from endogenous, e.g., naturally occurring, constant regions of the alpha chain. In some embodiments, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some embodiments, the anti-gp100 TCR comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some embodiments, the anti-gp100 TCR comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-gp100 TCR comprises a beta chain CDR3 comprising an amino acid sequence as set forth in SEQ ID NO: 10. In some embodiments, the anti-gp100 TCR comprises a beta chain constant region present in the beta chain amino acid sequence set forth in SEQ ID NO: 2. In some embodiments, the anti-gp100 TCR encoded by the first nucleotide further comprises a beta constant region that is different from endogenous, e.g., naturally occurring, constant regions of the beta chain. In some embodiments, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain embodiments, the anti-gp100 TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some embodiments, the anti-gp100 TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-gp100 TCR comprises an alpha chain CDR3 comprising an amino acid sequence as set forth in SEQ ID NO: 7. In some embodiments, the anti-gp100 TCR comprises an alpha chain comprising the amino acid sequence set forth in SEQ ID NO: 1.

In certain embodiments, the anti-gp100 TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some embodiments, the anti-gp100 TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-gp100 TCR comprises a beta chain CDR3 comprising an amino acid sequence as set forth in SEQ ID NO: 10. In some embodiments, the anti-gp100 TCR comprises a beta chain comprising the amino acid sequence set forth in SEQ ID NO: 2.

In some embodiments, the anti-gp100 TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

II.B.2. Epitopes

In some embodiments, the anti-gp100 TCR binds the same epitope as a reference TCR. In some embodiments, the anti-gp100 TCR binds to an epitope of gp100 comprising the amino acid sequence set forth in SEQ ID NO: 13. In some embodiments, the anti-gp100 TCR binds to an epitope of gp100 consisting of an amino acid sequence as set forth in SEQ ID NO: 13. In some embodiments, the epitope consists of amino acid residues intron4 of gp100 (SEQ ID NO: 52), e.g., "gp100-intron4."

In certain embodiments, the epitope is complexed with an HLA class I molecule. In some embodiments, the HLA class 1 molecule is selected from an HLA-A, HLA-B, and HLA-C allele. In some embodiments, the HLA class 1 molecule is selected from an HLA-E, HLA-F, and HLA-G allele. In certain embodiments, the HLA class 1 molecule is an HLA-A allele. In certain embodiments, the HLA class 1 molecule is an HLA-B allele. In certain embodiments, the HLA class 1 molecule is an HLA-C allele.

Many HLA-A, HLA-B, and HLA-C alleles are known in the art, and any of the known alleles can be used in the present disclosure. An updated list of HLA alleles is available at hla.alleles.org/ (last visited on Feb. 27, 2019). In some embodiments, the HLA class 1 molecule is an HLA-A allele selected from an HLA-A*01, an HLA-A*02, an HLA-A*03, an HLA-A*11, an HLA-A*23, an HLA-A*24, an HLA-A*25, an HLA-A*26, an HLA-A*29, an HLA- A*30, an HLA-A*31, an HLA-A*32, an HLA-A*33, an HLA-A*34, an HLA-A*36, an HLA-A*43, an HLA-A*66, an HLA-A*68, an HLA-A*69, an HLA-A*74, and an HLA-A*80. In certain embodiments, the HLA-A allele is an HLA-A*24:01 allele. In certain embodiments, the HLA-A allele is an HLA-A*24:02 allele. In certain embodiments, the HLA-A allele is an HLA-A*24:03 allele. In certain embodiments, the HLA-A allele is an HLA-A*24:11 allele. In certain embodiments, the HLA-A allele is an HLA-A*24:23 allele. In certain embodiments, the HLA-A allele is an HLA-A*24:24 allele. In certain embodiments, the HLA-A allele is an HLA-A*24:25 allele. In certain embodiments, the HLA-A allele is an HLA-A*24:26 allele.

In certain embodiments, the HLA class 1 molecule is an HLA-A allele selected from the group consisting of HLA-A*24:02:01:01, HLA-A*24:02:01:02, HLA-A*24:02:01:03, HLA-A*24:02:01:04, HLA-A*24:02:01:05, HLA-A*24:02:01:06, HLA-A*24:02:01:07, HLA-A*24:02:01:08, HLA-A*24:02:01:09, HLA-A*24:02:01:10, HLA-A*24:02:01:11, HLA-A*24:02:01:12, HLA-A*24:02:01:13, HLA-A*24:02:01:14, HLA-A*24:02:01:15, HLA-A*24:02:01:16, HLA-A*24:02:01:17, HLA-A*24:02:01:18, HLA-A*24:02:01:19, HLA-A*24:02:01:20, HLA-A*24:02:02, HLA-A*24:02:03, HLA-A*24:02:04, HLA-A*24:02:05, HLA-A*24:02:06, HLA-A*24:02:07, HLA-A*24:02:08, HLA-A*24:02:09, HLA-A*24:02:10, HLA-A*24:02:100, HLA-A*24:02:101, HLA-A*24:02:102, HLA-A*24:02:103, HLA-A*24:02:104, HLA-A*24:02:105, HLA-A*24:02:106, HLA-A*24:02:107, HLA-A*24:02:108, HLA-A*24:02:109, HLA-A*24:02:11, HLA-A*24:02:110, HLA-A*24:02:111, HLA-A*24:02:112, HLA-A*24:02:113, HLA-A*24:02:114, HLA-A*24:02:115, HLA-A*24:02:12, HLA-A*24:02:13, HLA-A*24:02:14, HLA-A*24:02:15, HLA-A*24:02:16, HLA-A*24:02:17, HLA-A*24:02:18, HLA-A*24:02:19, HLA-A*24:02:20, HLA-A*24:02:21, HLA-A*24:02:22, HLA-A*24:02:23, HLA-A*24:02:24, HLA-A*24:02:25, HLA-A*24:02:26, HLA-A*24:02:27, HLA-A*24:02:28, HLA-A*24:02:29, HLA-A*24:02:30, HLA-A*24:02:31, HLA-A*24:02:32, HLA-A*24:02:33, HLA-A*24:02:34, HLA-A*24:02:35, HLA-A*24:02:36, HLA-A*24:02:37, HLA-A*24:02:38, HLA-A*24:02:39, HLA-A*24:02:40, HLA-A*24:02:41, HLA-A*24:02:42, HLA-A*24:02:43, HLA-A*24:02:44, HLA-A*24:02:45, HLA-A*24:02:46, HLA-A*24:02:47, HLA-A*24:02:48, HLA-A*24:02:49, HLA-A*24:02:50, HLA-A*24:02:51, HLA-A*24:02:52, HLA-A*24:02:53, HLA-A*24:02:54, HLA-A*24:02:55, HLA-A*24:02:56, HLA-A*24:02:57, HLA-A*24:02:58, HLA-A*24:02:59, HLA-A*24:02:60, HLA-A*24:02:61, HLA-A*24:02:62, HLA-A*24:02:63, HLA-A*24:02:64, HLA-A*24:02:65, HLA-A*24:02:66, HLA-A*24:02:67, HLA-A*24:02:68, HLA-A*24:02:69, HLA-A*24:02:70, HLA-A*24:02:71, HLA-A*24:02:72, HLA-A*24:02:73, HLA-A*24:02:74, HLA-A*24:02:75, HLA-A*24:02:76, HLA-A*24:02:77, HLA-A*24:02:78, HLA-A*24:02:79, HLA-A*24:02:80, HLA-A*24:02:81, HLA-A*24:02:82, HLA-A*24:02:83, HLA-A*24:02:84, HLA-A*24:02:85, HLA-A*24:02:86, HLA-A*24:02:87, HLA-A*24:02:88, HLA-A*24:02:89, HLA-A*24:02:90, HLA-A*24:02:91, HLA-A*24:02:92, HLA-A*24:02:93, HLA-A*24:02:94, HLA-A*24:02:95, HLA-A*24:02:96, HLA-A*24:02:97, HLA-A*24:02:98, and HLA-A*24:02:99. In some embodiments, the HLA class 1 molecule is an HLA-A allele selected from the group consisting of HLA-A*24:03:01:01, HLA-A*24:03:01:02, HLA-A*24:03:02, HLA-A*24:03:03, HLA-A*24:03:04, HLA-A*24:04, HLA-A*24:05:01, HLA-A*24:05:02, HLA-A*24:06, HLA-A*24:07:01, HLA-A*24:07:02, HLA- A*24:08, HLA-A*24:09, HLA-A*24:100, HLA-A*24:101, HLA-A*24:102, HLA-A*24:103, HLA-A*24:104, HLA-A*24:105, HLA-A*24:106, HLA-A*24:107, HLA-A*24:108, HLA-A*24:109, HLA-A*24:10:01, HLA-A*24:10:02, HLA-A*24:110, HLA-A*24:111, HLA-A*24:112, HLA-A*24:113, HLA-A*24:114, HLA-A*24:115, HLA-A*24:116, HLA-A*24:117, HLA-A*24:118, HLA-A*24:119, HLA-A*24:11, HLA-A*24:120, HLA-A*24:121, HLA-A*24:122, HLA-A*24:123, HLA-A*24:124, HLA-A*24:125, HLA-A*24:126, HLA-A*24:127, HLA-A*24:128, HLA-A*24:129, HLA-A*24:130, HLA-A*24:131, HLA-A*24:132, HLA-A*24:133, HLA-A*24:134, HLA-A*24:135:01, HLA-A*24:135:02, HLA-A*24:136, HLA-A*24:137, HLA-A*24:138, HLA-A*24:139, HLA-A*24:13:01, HLA-A*24:13:02, HLA-A*24:140, HLA-A*24:141, HLA-A*24:142:01, HLA-A*24:142:02, HLA-A*24:143, HLA-A*24:144, HLA-A*24:145, HLA-A*24:146, HLA-A*24:147, HLA-A*24:148, HLA-A*24:149, HLA-A*24:14:01:01, HLA-A*24:14:01:02, HLA-A*24:14:01:03, HLA-A*24:15, HLA-A*24:150, HLA-A*24:151, HLA-A*24:152, HLA-A*24:153, HLA-A*24:154, HLA-A*24:155, HLA-A*24:156, HLA-A*24:157, HLA-A*24:158, HLA-A*24:159, HLA-A*24:160, HLA-A*24:161, HLA-A*24:162, HLA-A*24:163, HLA-A*24:164, HLA-A*24:165, HLA-A*24:166, HLA-A*24:167, HLA-A*24:168, HLA-A*24:169, HLA-A*24:17, HLA-A*24:170, HLA-A*24:171, HLA-A*24:172:01, HLA-A*24:172:02, HLA-A*24:173, HLA-A*24:174, HLA-A*24:175, HLA-A*24:176, HLA-A*24:177, HLA-A*24:178, HLA-A*24:179, HLA-A*24:18, HLA-A*24:180, HLA-A*24:181, HLA-A*24:182, HLA-A*24:183, HLA-A*24:184, HLA-A*24:185, HLA-A*24:186, HLA-A*24:187, HLA-A*24:188, HLA-A*24:189, HLA-A*24:19, HLA-A*24:190, HLA-A*24:191, HLA-A*24:192, HLA-A*24:193, HLA-A*24:194, HLA-A*24:195, HLA-A*24:196, HLA-A*24:197, HLA-A*24:198, HLA-A*24:199, HLA-A*24:200, HLA-A*24:201, HLA-A*24:202, HLA-A*24:203, HLA-A*24:204, HLA-A*24:205, HLA-A*24:206, HLA-A*24:207:01, HLA-A*24:207:02, HLA-A*24:208:01, HLA-A*24:208:02, HLA-A*24:209, HLA-A*24:20:01:01, HLA-A*24:20:01:02, HLA-A*24:210, HLA-A*24:212, HLA-A*24:213, HLA-A*24:214, HLA-A*24:215, HLA-A*24:216, HLA-A*24:217, HLA-A*24:218, HLA-A*24:219, HLA-A*24:21:01, HLA-A*24:21:02, HLA-A*24:21:03, HLA-A*24:22, HLA-A*24:220, HLA-A*24:221, HLA-A*24:222, HLA-A*24:223, HLA-A*24:224, HLA-A*24:225:01, HLA-A*24:225:02, HLA-A*24:226:01, HLA-A*24:226:02, HLA-A*24:227, HLA-A*24:228, HLA-A*24:229, HLA-A*24:23, HLA-A*24:230, HLA-A*24:231, HLA-A*24:232, HLA-A*24:233, HLA-A*24:234, HLA-A*24:235, HLA-A*24:236, HLA-A*24:237, HLA-A*24:238, HLA-A*24:239, HLA-A*24:24, HLA-A*24:240, HLA-A*24:241, HLA-A*24:242, HLA-A*24:243, HLA-A*24:244, HLA-A*24:245, HLA-A*24:246, HLA-A*24:247, HLA-A*24:248, HLA-A*24:249, HLA-A*24:25, HLA-A*24:250, HLA-A*24:251, HLA-A*24:252, HLA-A*24:253, HLA-A*24:254, HLA-A*24:255, HLA-A*24:256, HLA-A*24:257, HLA-A*24:258, HLA-A*24:259, HLA-A*24:26, HLA-A*24:260, HLA-A*24:261, HLA-A*24:262, HLA-A*24:263, HLA-A*24:264, HLA-A*24:265, HLA-A*24:266, HLA-A*24:267, HLA-A*24:268, HLA-A*24:269, HLA-A*24:27, HLA-A*24:270, HLA-A*24:271, HLA-A*24:272, HLA-A*24:273, HLA-A*24:274, HLA-A*24:275, HLA-A*24:276, HLA-A*24:277, HLA-A*24:278, HLA-A*24:279, HLA-A*24:28, HLA-A*24:280, HLA-A*24:281, HLA-A*24:282, HLA-A*24:283, HLA-A*24:284, HLA-A*24:285, HLA-A*24:286, HLA- A*24:287, HLA-A*24:288, HLA-A*24:289, HLA-A*24:
29, HLA-A*24:290, HLA-A*24:291, HLA-A*24:292,
HLA-A*24:293, HLA-A*24:294, HLA-A*24:295, HLA-
A*24:296, HLA-A*24:297, HLA-A*24:298, HLA-A*24:
299, HLA-A*24:30, HLA-A*24:300, HLA-A*24:301,
HLA-A*24:302, HLA-A*24:303, HLA-A*24:304, HLA-
A*24:305, HLA-A*24:306, HLA-A*24:307, HLA-A*24:
308, HLA-A*24:309, HLA-A*24:31, HLA-A*24:310:01,
HLA-A*24:310:02, HLA-A*24:311, HLA-A*24:312,
HLA-A*24:313:01, HLA-A*24:313:02, HLA-A*24:314,
HLA-A*24:315, HLA-A*24:316, HLA-A*24:317, HLA-
A*24:318, HLA-A*24:319, HLA-A*24:32, HLA-A*24:
320, HLA-A*24:321, HLA-A*24:322, HLA-A*24:323,
HLA-A*24:324, HLA-A*24:325, HLA-A*24:326, HLA-
A*24:327, HLA-A*24:328, HLA-A*24:329, HLA-A*24:
33, HLA-A*24:330, HLA-A*24:331, HLA-A*24:332,
HLA-A*24:333, HLA-A*24:334, HLA-A*24:335, HLA-
A*24:336, HLA-A*24:337, HLA-A*24:338, HLA-A*24:
339, HLA-A*24:34, HLA-A*24:340, HLA-A*24:341,
HLA-A*24:342, HLA-A*24:343, HLA-A*24:344, HLA-
A*24:345, HLA-A*24:346, HLA-A*24:347:01, HLA-
A*24:347:02, HLA-A*24:348, HLA-A*24:349, HLA-
A*24:35, HLA-A*24:350, HLA-A*24:351, HLA-A*24:
352, HLA-A*24:353, HLA-A*24:354, HLA-A*24:355,
HLA-A*24:356, HLA-A*24:357, HLA-A*24:358, HLA-
A*24:359, HLA-A*24:360, HLA-A*24:361, HLA-A*24:
362, HLA-A*24:363, HLA-A*24:364, HLA-A*24:365,
HLA-A*24:366, HLA-A*24:367, HLA-A*24:368, HLA-
A*24:369, HLA-A*24:36, HLA-A*24:37, HLA-A*24:370,
HLA-A*24:371, HLA-A*24:372, HLA-A*24:373, HLA-
A*24:374, HLA-A*24:375, HLA-A*24:376, HLA-A*24:
377, HLA-A*24:378, HLA-A*24:379, HLA-A*24:38,
HLA-A*24:380, HLA-A*24:381, HLA-A*24:382, HLA-
A*24:383, HLA-A*24:384, HLA-A*24:385, HLA-A*24:
386, HLA-A*24:387, HLA-A*24:388, HLA-A*24:389,
HLA-A*24:39, HLA-A*24:390, HLA-A*24:391, HLA-
A*24:392, HLA-A*24:393, HLA-A*24:394, HLA-A*24:
395, HLA-A*24:396, HLA-A*24:397, HLA-A*24:398,
HLA-A*24:399, HLA-A*24:400, HLA-A*24:401, HLA-
A*24:402, HLA-A*24:403, HLA-A*24:404, HLA-A*24:
405, HLA-A*24:406, HLA-A*24:407, HLA-A*24:408,
HLA-A*24:409, HLA-A*24:40, HLA-A*24:41, HLA-
A*24:410, HLA-A*24:411, HLA-A*24:412, HLA-A*24:
413, HLA-A*24:414, HLA-A*24:415, HLA-A*24:416,
HLA-A*24:417, HLA-A*24:418, HLA-A*24:419, HLA-
A*24:42, HLA-A*24:420, HLA-A*24:421, HLA-A*24:
422, HLA-A*24:423, HLA-A*24:424, HLA-A*24:425,
HLA-A*24:426, HLA-A*24:427, HLA-A*24:428, HLA-
A*24:429, HLA-A*24:43, HLA-A*24:430, HLA-A*24:
431, HLA-A*24:432, HLA-A*24:433, HLA-A*24:44,
HLA-A*24:45, HLA-A*24:46, HLA-A*24:47, HLA-A*24:
48, HLA-A*24:49, HLA-A*24:50, HLA-A*24:51, HLA-
A*24:52, HLA-A*24:53, HLA-A*24:54, HLA-A*24:55,
HLA-A*24:56, HLA-A*24:57, HLA-A*24:58, HLA-A*24:
59, HLA-A*24:60, HLA-A*24:61, HLA-A*24:62, HLA-
A*24:63, HLA-A*24:64, HLA-A*24:66, HLA-A*24:67,
HLA-A*24:68, HLA-A*24:69, HLA-A*24:70, HLA-A*24:
71, HLA-A*24:72, HLA-A*24:73, HLA-A*24:74:01,
HLA-A*24:74:02, HLA-A*24:75, HLA-A*24:76, HLA-
A*24:77, HLA-A*24:78, HLA-A*24:79, HLA-A*24:80,
HLA-A*24:81, HLA-A*24:82, HLA-A*24:83, HLA-A*24:
84, HLA-A*24:85, HLA-A*24:86, HLA-A*24:87, HLA-
A*24:88, HLA-A*24:89, HLA-A*24:90:01, HLA-A*24:
90:02, HLA-A*24:91, HLA-A*24:92, HLA-A*24:93,
HLA-A*24:94, HLA-A*24:95, HLA-A*24:96, HLA-A*24:
97, HLA-A*24:98, and HLA-A*24:99.

II.B.3. Bispecific T Cell Receptors (TCRs)

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein. In some embodiments, the first antigen-binding domain comprises a single chain variable fragment ("scFv").

In some embodiments, the second antigen-binding domain binds specifically to a protein expressed on the surface of a T cell. Any protein expressed on the surface of a T cell can be targeted by the bispecific antibody disclosed herein. In certain embodiments, the protein expressed on the surface of a T cell is not expressed by other cells. In some embodiments, the protein expressed on the surface of a T cell is expressed on the surface of one or more other human immune cells. In some embodiments, the protein expressed on the surface of a T cell is expressed on the surface of one or more other human immune cells, but it is not expressed on the surface of a human non-immune cell. In some embodiments, the second antigen-binding domain binds specifically to a protein expressed on the surface of a T cell selected from CD3, CD2, CD5, CD6, CD8, CD11a (LFA-1a), CD43, CD45, and CD53. In certain embodiments, the second antigen-binding domain binds specifically to CD3. In some embodiments, the second antigen-binding domain comprises an scFv.

In some embodiments, the first antigen-binding domain and the second antigen-binding domain are linked or associated by a covalent bond. In some embodiments, the first antigen-binding domain and the second antigen-binding domain are linked by a peptide bond.

II.C. Cells Expressing TCRs

Certain aspects of the present disclosure are directed to cells comprising a nucleic acid molecule disclosed herein, a vector disclosed herein, a recombinant TCR disclosed herein, a bispecific TCR disclosed herein, or any combination thereof. Any cell can be used in the present disclosure.

In certain embodiments, the cell expresses CD3. CD3 expression can be naturally occurring, e.g., the CD3 is expressed from a nucleic acid sequence that is endogenously expressed by the cell. For example, T cells and natural killer (NK) cells naturally express CD3. Thus, in some embodiments, the cell is a T cell or a natural killer cell. In certain embodiments, the cell is a T cell selected from a natural killer T (NKT) cell and an innate lymphoid cell (ILC).

In some embodiments, the T cell is isolated from a human subject. In some embodiments, the human subject is the same subject that will ultimately receive the T cell therapy. In other embodiments, the subject is a donor subject, wherein the donor subject is not the same subject that will receive the T cell therapy.

In some embodiments, the cell is a cell that does not naturally express CD3, wherein the cell has been modified to express CD3. In some embodiments, the cell comprises a transgene encoding CD3, wherein the transgene is expressed by the cell. In some embodiments, the cell comprises a transgene encoding a protein that activates expression of endogenous CD3 by the cell. In some embodiments, the cell comprises a transgene encoding a protein or siRNA that inhibits an inhibitor of CD3 expression in the cell. In some embodiments, the transgene is incorporated into the genome of the cell. In some embodiments, the transgene is not incorporated into the genome of the cell.

In some embodiments, the cell that is modified to express CD3 is isolated from a human subject. In some embodiments, the human subject is the same subject that will ultimately receive the cell therapy. In other embodiments, the subject is a donor subject, wherein the donor subject is not the same subject that will receive the cell therapy.

II.D. HLA Class I Molecules

Certain aspects of the present disclosure are directed to a HLA class I molecule complexed to a peptide, wherein the peptide comprises the amino acid sequence set forth in SEQ ID NO: 13. In some embodiments, he peptide consists of the amino acid sequence set forth in SEQ ID NO: 13.

In some embodiments, the HLA Class I molecule is an HLA-A, HLA-B, or an HLA-C. In some embodiments, the HLA Class I molecule is an HLA-E, HLA-F, or HLA-G. In some embodiments, the HLA class 1 molecule is an HLA-A allele selected from an HLA-A*01, an HLA-A*02, an HLA-A*03, an HLA-A*11, an HLA-A*23, an HLA-A*24, an HLA-A*25, an HLA-A*26, an HLA-A*29, an HLA-A*30, an HLA-A*31, an HLA-A*32, an HLA-A*33, an HLA-A*34, an HLA-A*36, an HLA-A*43, an HLA-A*66, an HLA-A*68, an HLA-A*69, an HLA-A*74, and an HLA-A*80. In certain embodiments, the HLA-A allele is an HLA-A*24:01 allele. In certain embodiments, the HLA-A allele is an HLA-A*24:02 allele. In certain embodiments, the HLA-A allele is an HLA-A*24:03 allele. In certain embodiments, the HLA-A allele is an HLA-A*24:11 allele. In certain embodiments, the HLA-A allele is an HLA-A*24:23 allele. In certain embodiments, the HLA-A allele is an HLA-A*24:24 allele. In certain embodiments, the HLA-A allele is an HLA-A*24:25 allele. In certain embodiments, the HLA-A allele is an HLA-A*24:26 allele. In some embodiments, the HLA allele is any HLA allele disclosed herein, e.g., supra.

In some embodiments, the HLA Class I molecule comprises an alpha chain and a β2m. In some embodiments, the alpha chain comprises an α1 domain, an α2 domain, an α3 domain. In some embodiments, the β2m comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 16. In some embodiments, the sequence of the alpha chain is selected from any of the HLA protein sequences available at hla.alleles.org (last visited Feb. 27, 2019).

In some embodiments, the HLA class I molecule is a monomer. In some embodiments, the HLA class I molecule is a dimer. In some embodiments, the HLA class I molecule is a multimer. In some embodiments, the HLA class I molecule is a trimer. In some embodiments, the HLA class I molecule is a tetramer. In some embodiments, the HLA class I molecule is a pentamer.

Certain aspects of the present disclosure are directed to antigen presenting cells (APCs) comprising any HLA class I molecule disclosed herein. In certain embodiments, the APC expressed the HLA class I molecule on the surface of the APC. In certain embodiments, the APC comprises more than one HLA class I molecule disclosed herein.

II.D. Vaccines

Certain aspects of the present disclosure a cancer vaccine comprising a peptide comprising an amino acid sequence as set forth in SEQ ID NO: 13. In some embodiments, the cancer vaccine comprises a peptide that consists of the amino acid sequence set forth in SEQ ID NO: 13. In some embodiments, the vaccine further comprises one or more excipient. In some embodiments, the vaccine further comprises one or more additional peptides. In some embodiments, the one or more additional peptides comprise one or more additional epitopes.

III. Methods of the Disclosure

Certain aspects of the present disclosure are directed to methods of treating a cancer in a subject in need thereof. Other aspects of the present disclosure are directed to methods of engineering an antigen-targeting cell. Other aspects of the present disclosure are directed to methods of enriching a target population of T cells obtained from a human subject.

III.A. Methods of Treating Cancer

Certain aspects of the present disclosure are directed to methods of treating a cancer in a subject in need thereof, comprising administering to the subject a nucleic acid molecule disclosed herein, a recombinant TCR disclosed herein, a bispecific TCR disclosed herein, an epitope disclosed herein, or an HLA class I molecule disclosed herein, or a vector or cell comprising any of the above.

In some embodiments, the cancer is selected from melanoma, bone cancer, renal cancer, prostate cancer, breast cancer, colon cancer, lung cancer, cutaneous or intraocular malignant melanoma, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In some embodiments, the cancer melanoma.

In some embodiments, the cancer is relapsed. In some embodiments, the cancer is refractory. In some embodiments, the cancer is advanced. In some embodiments, the cancer is metastatic.

In some embodiments, the methods disclosed herein treat a cancer in a subject. In some embodiments, the methods disclosed herein reduce the severity of one or more symptom of the cancer. In some embodiments, the methods disclosed herein reduce the size or number of a tumor derived from the cancer. In some embodiments, the methods disclosed herein increase the overall survival of the subject, relative to a subject not provided the methods disclosed herein. In some embodiments, the methods disclosed herein increase the progressive-free survival of the subject, relative to a subject not provided the methods disclosed herein. In some embodiments, the methods disclosed herein lead to a partial response in the subject. In some embodiments, the methods disclosed herein lead to a complete response in the subject.

In some embodiments, the methods disclosed herein comprise treating a cancer in a subject in need thereof, comprising administering to the subject a cell described herein, wherein the cell comprises a nucleic acid molecule disclosed herein, a vector disclosed herein, a recombinant TCR disclosed herein, and/or a bispecific antibody disclosed herein. In some embodiments, the cell is a T cell. In some embodiments, the cell is a cell that is modified to express CD3.

In some embodiments, the cell, e.g., a T cell, is obtained from the subject. In some embodiments, the cell, e.g., a T cell, is obtained from a donor other than the subject.

In some embodiments, the subject is preconditioned prior to administering the cells. The preconditioning can comprise any substance that promotes T cell function and/or survival. In some embodiments, the preconditioning comprises administering to the subject a chemotherapy, a cytokine, a protein, a small molecule, or any combination thereof. In some embodiments, the preconditioning comprises administering an interleukin. In some embodiments, the preconditioning comprises administering IL-2, IL-4, IL-7, IL-9, IL-15, IL-21, or any combination thereof. In some embodiments, the preconditioning comprises administering cyclophosphamide, fludarabine, or both. In some embodiments, the preconditioning comprises administering vitamin C, an AKT inhibitor, ATRA (vesanoid, tretinoin), rapamycin, or any combination thereof.

III.B. Methods of Engineering an Antigen-Targeting Cell

Certain aspects of the present disclosure are directed to methods of engineering an antigen-targeting cell. In some embodiments, the antigen is a gp100 antigen. In some embodiments, the method comprises transducing a cell with a nucleic acid molecule disclosed herein or a vector disclosed herein. The cell can be any cell described herein. In some embodiments, the cell is a T cell described herein. In some embodiments, the cell is a cell that is modified to express CD3, as described herein. In some embodiments, the cell, e.g., the T cell, is obtained from a subject in need of a T cell therapy. In some embodiments, the cell is obtained from a donor other than the subject in need of the T cell therapy. In some embodiments, the cell is a T cell or a natural killer cell.

III.C. Methods of Enriching a Target Population of T Cells

Certain aspects of the present disclosure are directed to methods of enriching a target population of T cells obtained from a human subject. In some embodiments, the method comprises contacting the T cells with an HLA class I molecule disclosed herein. In some embodiments, the method comprises contacting the T cells with an APC disclosed herein. In some embodiments, following the contacting, the enriched population of T cells comprises a higher number of T cells capable of binding the HLA class I molecule relative to the number of T cells capable of binding the HLA class I molecule prior to the contacting.

In some embodiments, the method comprises contacting the T cells in vitro with a peptide, wherein the peptide comprises the amino acid sequence set forth in SEQ ID NO: 13. In some embodiments, the method comprises contacting the T cells in vitro with a peptide, wherein the peptide consists of the amino acid sequence set forth in SEQ ID NO: 13. In some embodiments, following the contacting, the enriched population of T cells comprises a higher number of T cells capable of binding the HLA class I molecule relative to the number of T cells capable of binding the HLA class I molecule prior to the contacting.

Some aspects of the present disclosure are directed to a method of selecting a T cell capable of targeting a tumor cell. In some embodiments, the method comprises contacting a population of isolated T cells in vitro with a peptide, wherein the peptide consists of an amino acid sequence as set forth in SEQ ID NO: 13. In some embodiments, the T cells are obtained from a human subject.

The T cells obtained from the human subject can be any T cells disclosed herein. In some embodiments, the T cells obtained from the human subject are tumor infiltrating lymphocytes (TIL).

In some embodiments, the method further comprises administering to the human subject the enriched T cells. In some embodiments, the subject is preconditioned prior to receiving the T cells, as described herein.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1

Figure 2:
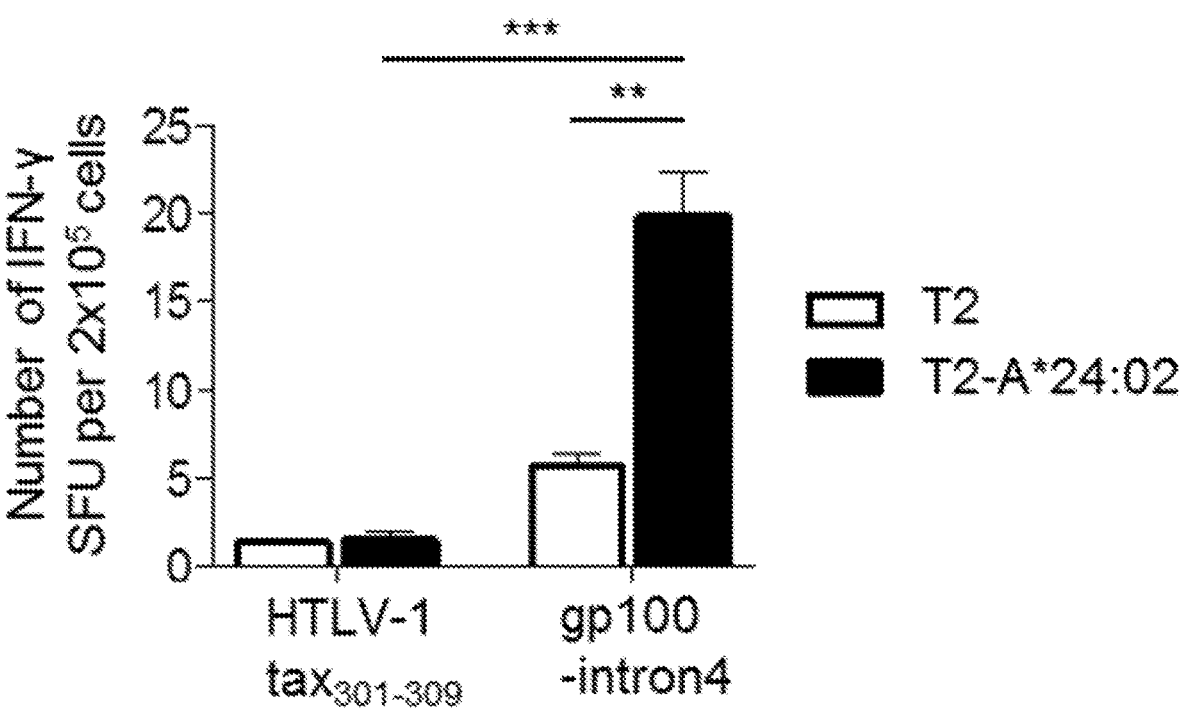
FIG. 2 is a bar graph illustrating the functional assessment of A*24:02/gp100-intron4 multimer-positive melanoma TILs. IFN-γ production by A*24:02-positive TILs in an HLA-A*24:02-restricted peptide-specific manner. The TILs were employed as responder cells in IFN-γ ELISPOT analysis. HLA-A*24:02 transduced T2 cells (T2-A*24:02) were generated. T2 or T2-A*24:02 cells pulsed with the indicated peptide were used as stimulator cells. The HTLV-1 tax$_{301-309}$ peptide was employed as a control. Experiments were carried out in triplicate, and error bars depict standard deviation (SD). P<0.01, *P<0.001.

TILs were isolated from a metastatic melanoma patient, then polyclonally expanded in vitro, and their gp100 antigen specificity for HLA-A*24:02 allele was examined. The combination of structure-based analysis using peptide/HLA (pHLA) multimers and functional analysis has been used to measure antigen-specific T cell responses. We stained the T cells using pHLA multimer with gp100-intron4 peptide that was previously known (FIG. 1). The TILs showed positivity for A*24:02/gp100-intron4 multimer. The multimer-positive T cells secreted detectable IFN-γ in an HLA-restricted peptide-specific manner according to ELISPOT analysis (FIG. 2).

Figure 3:
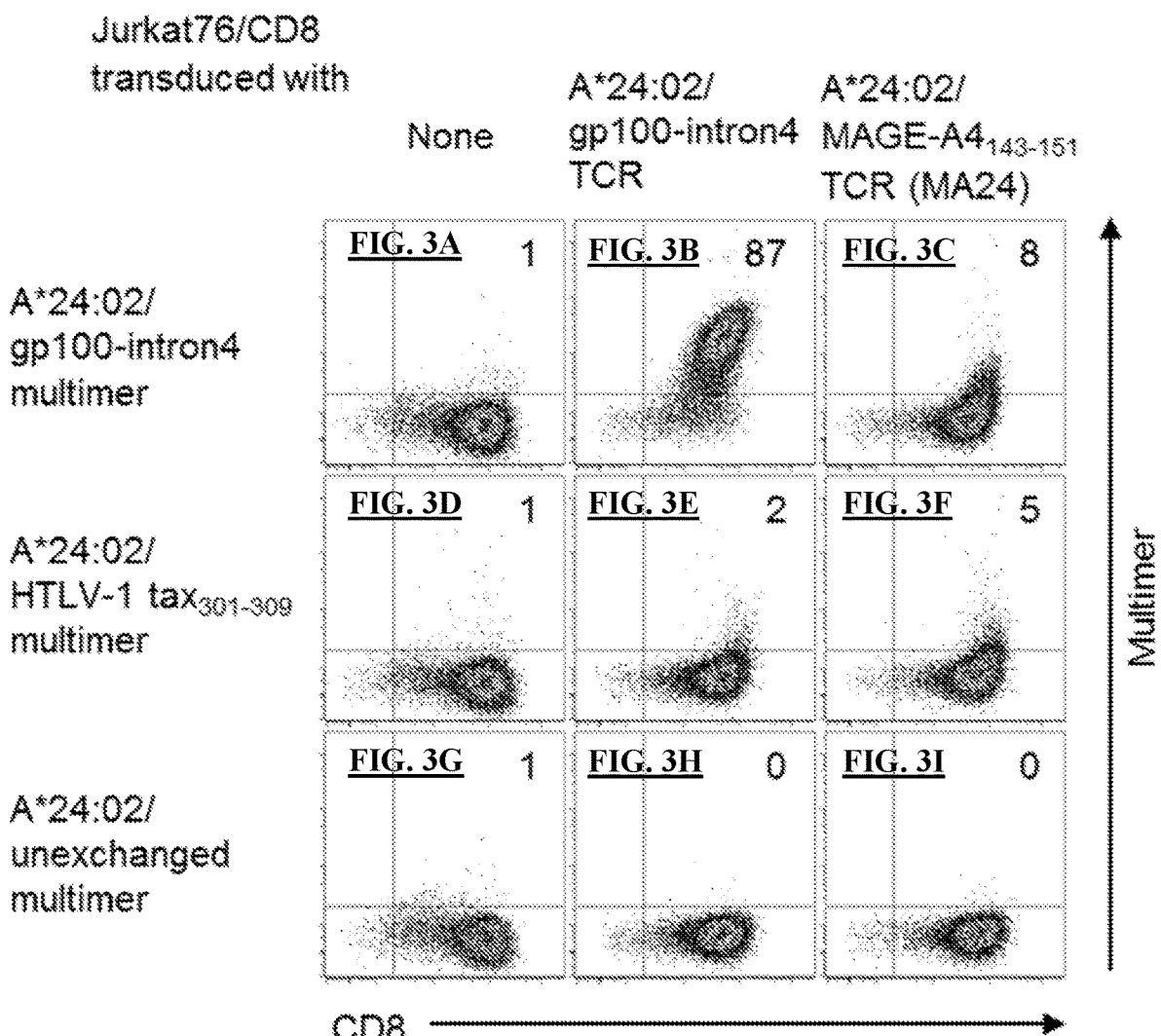
FIGS. 3A-3I are graphical representations of positive staining of Jurkat 76/CD8 cells transduced with A*24:02/gp100-intron4 TCR genes with a cognate multimer. Jurkat 76/CD8 cells transduced with the A*24:02/gp100-intron4 TCR (FIGS. 3B, 3E, and 3H) were stained with the A*24:02/gp100-intron4 multimer (FIG. 3B). The A*24:02/HTLV-1 tax$_{301-309}$ multimer (FIGS. 3D, 3E, and 3F), A*24:02/unexchanged multimer (FIGS. 3G, 3H, and 3I), and Jurkat 76/CD8 cells transduced with A*24:02/MAGE-A4$_{143-151}$ TCR (clone MA24.
Figure 4:
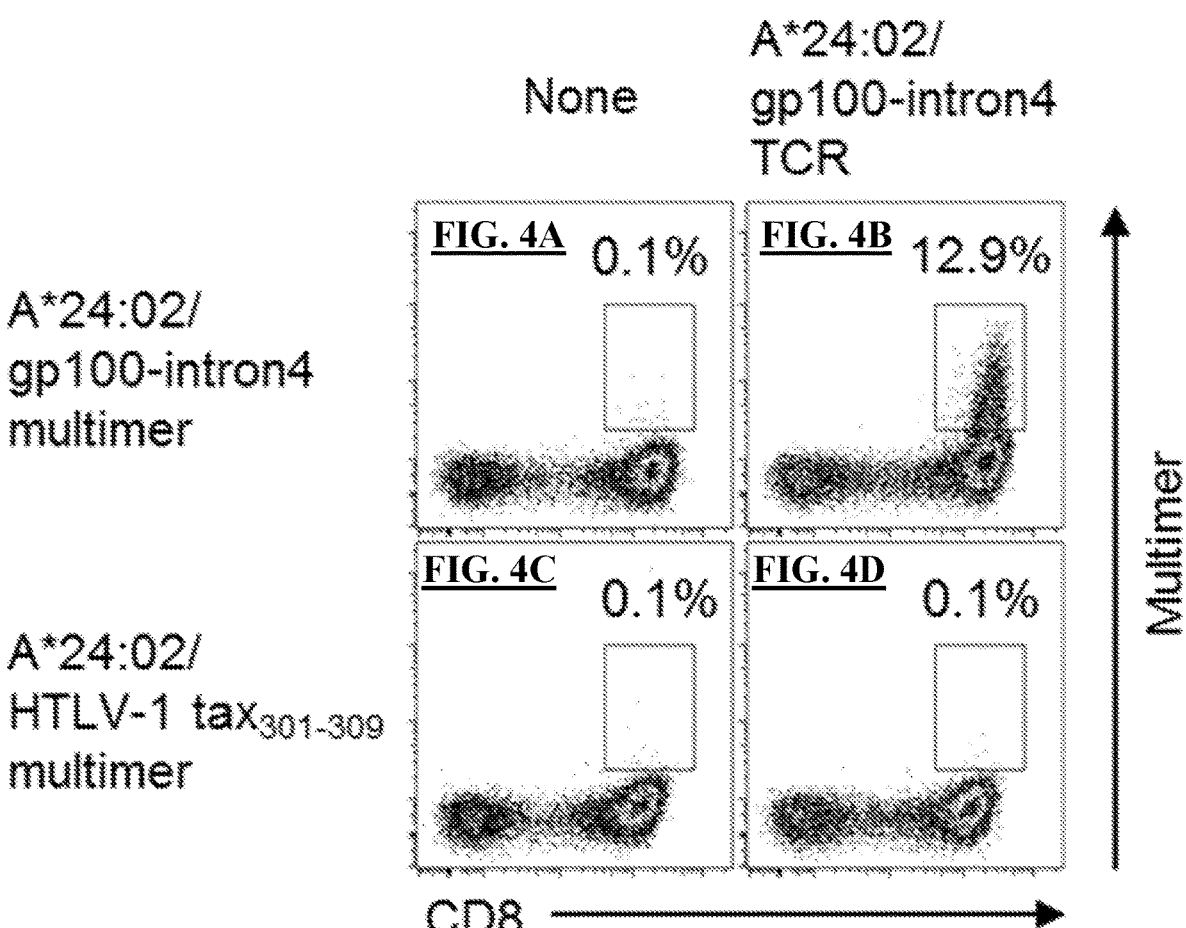
FIGS. 4A-4D are graphical representations of positive staining of human primary T cells transduced with A*24:02/gp100-intron4 TCR genes (FIGS. 4B and 4D) with a cognate multimer. Primary T cells transduced with the A*24:02/gp100-intron4 TCR were stained with the A*24:02/gp100-intron4 (FIG. 4B) or A*24:02/HTLV-1 tax$_{301-309}$ control multimer (FIG. 4D). Untransduced primary T cells were employed as negative controls (FIGS. 4A and 4C). The percentage of multimer$^+$ CD8$^+$ T cells is shown.
Figure 5:
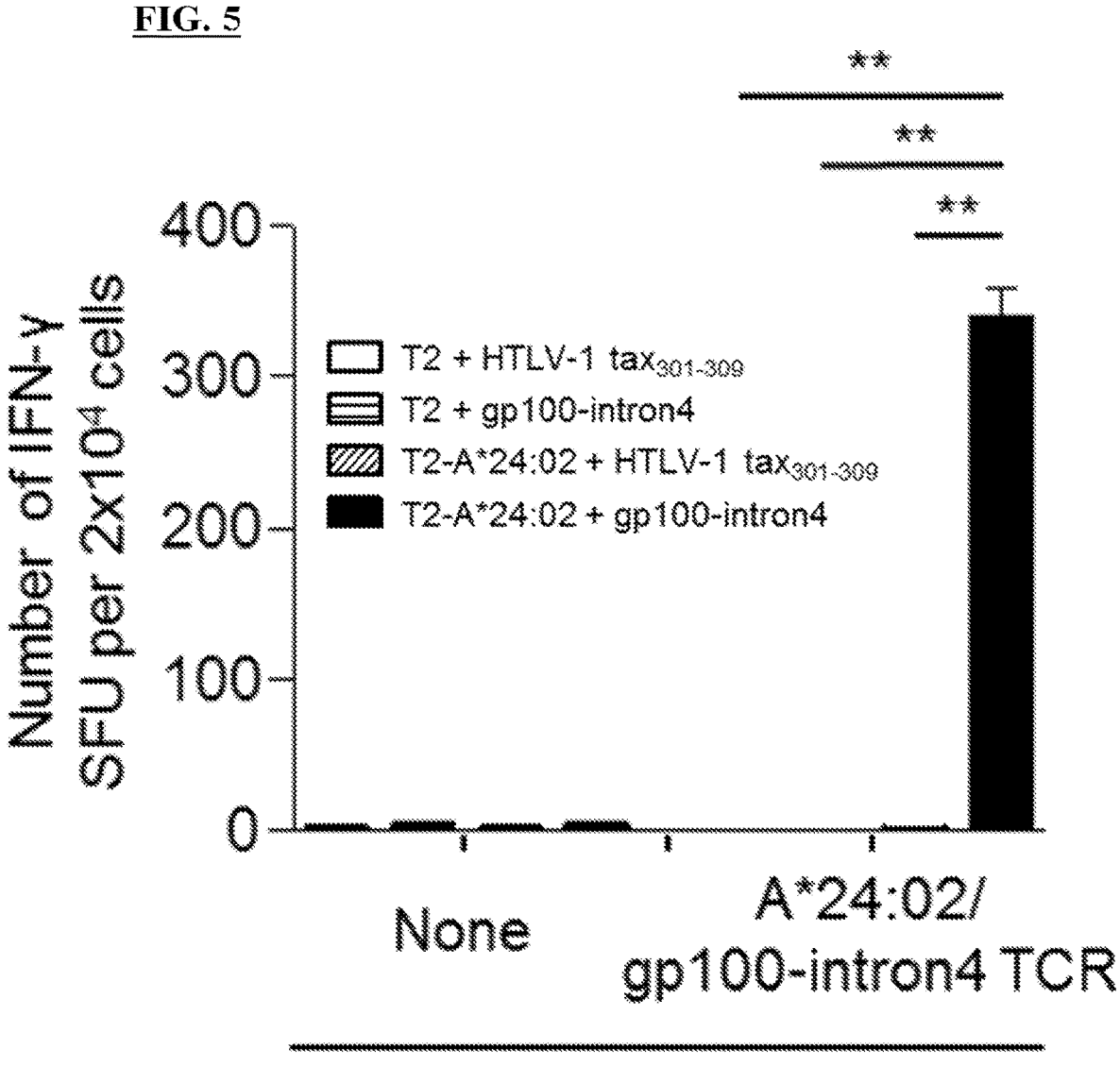
FIG. 5 is a bar graph illustrating that human primary T cells transduced with A*24:02/gp100-intron4 TCR genes react strongly with the cognate peptide presented by the target class I molecule. Primary T cells transduced with A*24:02/gp100-intron4 TCR genes or untransduced primary T cells (x-axis) were used as responder cells in IFN-γ ELISPOT analysis. T2 or T2-A*24:02 cells pulsed with the gp100-intron4 or HTLV-1 tax$_{301-309}$ peptide (control) were used as stimulator cells. Experiments were carried out in triplicate, and error bars depict SD. **P<0.01.
Figures 6A, 6B:
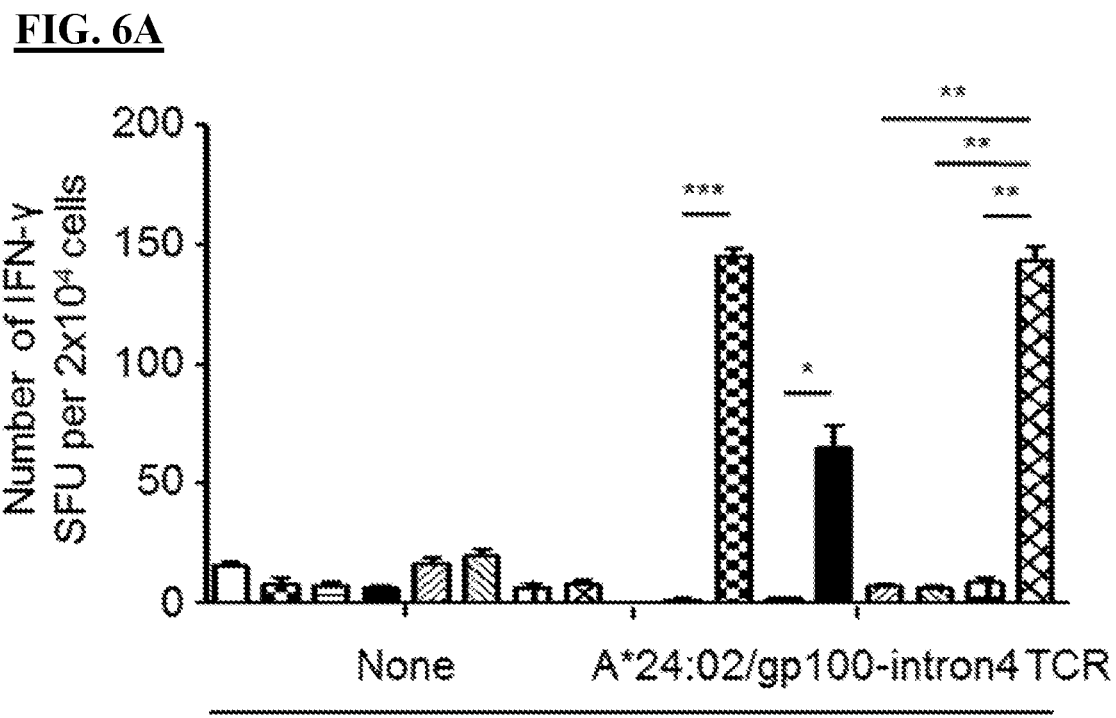
FIG. 6A is a graphical representation illustrating that primary T cells transduced with A*24:02/gp100-intron4 TCR genes recognize tumor cells. Primary T cells transduced with A*24:02/gp100-intron4 TCR genes or untransduced primary T cells were employed as responder cells in IFN-γ ELISPOT analysis. Malme-3M, SK-MEL-28, and A375 cells that were either untransduced or transduced with HLA-A*24:02 and/or gp100-intron4, as indicated in FIG. 6B (legend for FIG. 6A), were employed as stimulator cells.

The multimer-positive antitumor T cells were collected and their TCR genes were molecularly cloned (FIG. 3; SEQ ID NOs: 1 and 2). The antigen specificity and functional reactivity of the cloned TCR were verified by multimer staining and ELISPOT assay of TCR-reconstituted T cells. When reconstituted on primary T cells, A*24:02/gp100-intron4 TCR-transduced T cells were successfully stained with the cognate multimer (FIG. 4) and strongly reacted with the gp100-intron4 peptide presented by surface A*24:02 molecules (FIG. 5). Importantly, these cells were able to recognize A*24:02-matched and peptide-unpulsed tumor cells naturally expressing the gp100 gene (FIG. 6). Although both the Malme-3M and SK-MEL-28 melanoma cell lines are negative for A*24:02, they express the gp100 gene endogenously. When A*24:02 molecules were ectopically expressed, both melanoma cell lines were successfully recognized by A*24:02/gp100-intron4 TCR-transduced T cells. Moreover, A375 melanoma cells, which lack endogenous expression of both A*24:02 and gp100, became reactive to A*24:02/gp100-intron4 TCR-transduced T cells only when both the A*24:02 and gp100-intron4 genes (but not either of the single genes) were transduced (FIGS. 6-8). These results clearly demonstrate that the A*24:02/gp100-intron4 TCR-transduced T cells were sufficiently avid to recognize tumor cells and that the cloned A*24:02/gp100-intron4 TCR was tumor-reactive.

Gp100 is one of the shared antigens that have been promising and extensively studied in bispecific T cell engager (BiTE) therapy, and clinical trials targeting gp100 are ongoing in patients with metastatic uveal melanoma, using IMCgp100 which is a bispecific biologic comprised of a soluble TCR recognizing the gp100 antigen fused to a scFV anti-CD3 that redirects T cell lysis of melanoma cells expressing gp100 in the context of HLA-A*02:01 molecules. The use of the newly cloned tumor-reactive A*24: 02-restricted gp100-intron4 TCR genes may widen the applicability of BiTE therapy targeting gp100 beyond HLA-A*02:01-positive cancer patients.

Methods

Cell Samples

Peripheral blood samples were obtained from healthy donors. Mononuclear cells were obtained via density gradient centrifugation (Ficoll-Paque PLUS; GE Healthcare). K562 is an erythroleukemic cell line with defective HLA expression. T2 is an HLA-A*02:01$^+$ T cell leukemia/B-LCL hybrid cell line. Jurkat 76 is a T cell leukemic cell line lacking TCR and CD8 expression. Melme-3M cell line was grown in IMDM supplemented with 20% FBS and 50 µg/ml gentamicin (Invitrogen). SK-MEL-28 and A375 cell lines were grown in DMEM supplemented with 10% FBS and 50 µg/ml gentamicin (Invitrogen). The K562, T2, and Jurkat 76 cell lines were cultured in RPMI 1640 supplemented with 10% FBS and 50 µg/ml gentamicin. TILs isolated from a metastatic melanoma patient were grown in vitro.

Peptides

Synthetic peptides were dissolved to 50 µg/ml in DMSO. Peptides used were A*24:02-restricted gp100-intron4 (VYFFLPDHL; SEQ ID NO: 13) and HTLV-1 tax$_{301-309}$ (SFHSLHLLF; SEQ ID NO: 194) peptides. HTLV-1 tax$_{301-309}$ peptide was utilized as a negative control.

Genes

HLA-A*24:02 gene was fused with a truncated version of the human nerve growth factor receptor (ΔNGFR) via the internal ribosome entry site. ΔNGFR-transduced cells were isolated using anti-NGFR mAb. The full-length gp100 gene was purchased from Dharmacon (Lafayette, CO). Genomic DNA of gp100 was isolated from SK-MEL-28 using Pure-Link Genomic DNA Mini Kit (Invitrogen). TCR genes were cloned by 5'-rapid amplification of cDNA ends (RACE) PCR using a SMARTer RACE cDNA amplification kit (Takara Bio). The 5'-RACE PCR products were cloned into a retrovirus vector and sequenced. All genes were cloned into the pMX retrovirus vector and transduced using the 293GPG cell-based retrovirus system.

Transfectants

Jurkat 76/CD8 cells were transduced with individual TCRα and TCRβ genes. The Jurkat 76/CD8-derived TCR transfectants were purified (>95% purity) using CD3 Microbeads (Miltenyi Biotec). The K562-based artificial APCs individually expressing various HLA class I genes as a single HLA allele in conjunction with CD80 and CD83 have been reported previously (Butler and Hirano, *Immunol. Rev.* 257:191-209 (2014); Hirano et al., *Clin. Cancer Res.* 12:2967-75 (2006)). PG13-derived retrovirus supernatants were used to transduce TCR genes into human primary T cells. TransIT293 (Mirus Bio) was used to transfect TCR genes into the 293GPG cell line. Gp100⁻ A375 cells were retrovirally transduced with exons 1, 2, and 3 and intron 4 of the gp100 gene to generate A375/gp100-intron4 cells. The expression of transduced gp100-intron4 was evaluated by flow cytometry after staining with an anti-gp100 mAb (clone 7E3; LifeSpan Biosciences). HLA-A*24:02⁻ Malme-3M, SK-MEL-28, and A375 cells were retrovirally transduced with HLA-A*24:02 to generate Malme-3M/A*24:02, SK-MEL-28/A*24:02, and A375/A*24:02 cells, respectively. HLA-A*24:02 gene was tagged with the ΔNGFR gene as described above, and the ΔNGFR⁺ cells were purified (>95% purity) and used in subsequent experiments. The ΔNGFR gene alone was retrovirally transduced as a control.

Flow Cytometry and Cell Sorting

Cell surface molecules were stained with a PC5-conjugated anti-CD8 monoclonal antibody (mAb) (clone B9.11; Beckman Coulter), FITC-conjugated anti-NGFR (clone ME20.4; Biolegend), and APC/Cy7-conjugated anti-CD3 (clone UCHT1; Biolegend). Dead cells were discriminated with the LIVE/DEAD Fixable Aqua Dead Cell Stain kit (Life Technologies). For intracellular staining, cells were fixed and permeabilized by using a Cytofix/Cytoperm kit (BD Biosciences). Stained cells were analyzed with flow cytometry (BD Biosciences), and data analysis was performed using FlowJo (Tree Star). Cell sorting was conducted using a FACS Aria II (BD Bioscience).

Cytokine ELISPOT Analysis

IFN-γ ELISPOT assays were conducted. PVDF plates (Millipore, Bedford, MA) were coated with the capture mAb (1-D1K; MABTECH, Mariemont, OH), and T cells were incubated with 2×10⁴ target cells per well in the presence or absence of a peptide for 20-24 hours at 37° C. The plates were subsequently washed and incubated with a biotin-conjugated detection mAb (7-B6-1; MABTECH). HRP-conjugated SA (Jackson ImmunoResearch) was then added, and IFN-γ spots were developed. The reaction was stopped by rinsing thoroughly with cold tap water. ELISPOT plates were scanned and counted using an ImmunoSpot plate reader and ImmunoSpot version 5.0 software (Cellular Technology Limited, Shaker Heights, OH).

Expansion of CD8⁺ TILs in an HLA-Restricted Peptide-Specific Manner

CD8⁺ TILs were purified through negative magnetic selection using the CD8⁺ T Cell Isolation Kit (Miltenyi Biotec). A*24:02-artificial APCs were pulsed with 10 µg/mL the gp100-intron4 peptide for 6 hours. The artificial APCs were then irradiated at 200 Gy, washed, and added to the TILs at an effector to target (E:T) ratio of 20:1. Starting on the next day, 10 IU/ml IL-2 (Novartis), 10 ng/ml IL-15 (Peprotech), and 30 ng/ml IL-21 (Peprotech) were added to the cultures every three days.

Expansion of Primary CD8⁺ T Cells Transduced with the Cloned TCR

CD3⁺ T cells were purified through negative magnetic selection using a Pan T Cell Isolation Kit (Miltenyi Biotec). Purified T cells were stimulated with artificial APC/mOKT3 irradiated with 200 Gy at an E:T ratio of 20:1. Starting on the next day, activated T cells were retrovirally transduced with the cloned TCR genes via centrifugation for 1 hour at 1,000 g at 32° C. for 3 consecutive days. On the following day, 100 IU/ml IL-2 and 10 ng/ml IL-15 were added to the TCR-transduced T cells. The culture medium was replenished every 2-3 days.

Production of Human Cell-Based pHLA Multimers

The affinity-matured HLA class I gene was engineered to carry a Glu (E) residue in lieu of the Gln (Q) residue at position 115 of the α2 domain and a mouse K$^b$ gene-derived α3 domain instead of the HLA class I α3 domain. By fusing the extracellular domain of the affinity-matured HLA class I gene with a Gly-Ser (GS) flexible linker followed by a 6× His tag, we generated the soluble HLA class I$^{Q115E}$-K$^b$ gene. HEK293T cells were individually transduced with various soluble HLA class I$^{Q115E}$-K$^b$ genes along with the β2m gene using the 293GPG cell-based retrovirus system. Stable HEK293T cells ectopically expressing soluble affinity-matured class $I^{Q115E}$-$K^b$ were grown until confluent, and the medium was then changed. Forty-eight hours later, the conditioned medium was harvested and immediately used or frozen until use. The soluble HLA class $I^{Q115E}$-$K^b$-containing supernatant produced by the HEK293T transfectants was mixed with 100-1000 µg/ml of class I-restricted peptide of interest overnight at 37° C. for in vitro peptide exchange. Soluble monomeric class $I^{Q115E}$-$K^b$ loaded with the peptide was dimerized using an anti-His mAb (clone AD1.1.10; Abcam) conjugated to a fluorochrome such as phycoerythrin (PE) at a 2:1 molar ratio for 2 hours at room temperature or overnight at 4° C. The concentration of functional soluble HLA class $I^{Q115E}$-$K^b$ molecules was measured by specific ELISA using an anti-pan class I mAb (clone W6/32, in-house) and an anti-His tag biotinylated mAb (clone AD1.1.10, R&D systems) as capture and detection Abs, respectively.

pHLA Multimer Staining

T cells (1×10⁵) were incubated for 30 minutes at 37° C. in the presence of 50 nM dasatinib (LC laboratories). The cells were then washed and incubated with 5-10 µg/ml of multimer for 30 minutes at room temperature, and R-phycoerythrin-conjugated AffiniPure Fab fragment goat anti-mouse IgG1 (Jackson ImmunoResearch Laboratories) was added for 15 minutes at 4° C. Next, the cells were washed three times and costained with an anti-CD8 mAb for 15 minutes at 4° C. Dead cells were finally discriminated using the LIVE/DEAD Fixable Dead Cell Stain kit.

Statistical Analysis

Statistical analysis was performed using GraphPad Prism 5.0e. To determine whether two groups were significantly different for a given variable, we conducted an analysis using Welch's t test (two-sided). P values<0.05 were considered significant.

---

The invention claimed is:

1. A nucleic acid molecule comprising (i) a first nucleotide sequence encoding a recombinant T cell receptor (TCR) or an antigen binding portion thereof that specifically binds human gp100 ("anti-gp100 TCR"); and (ii) a second nucleotide sequence, wherein the second nucleotide sequence or the polypeptide encoded by the second nucleotide sequence inhibits the expression of an endogenous TCR, wherein the anti-gp100 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3;

wherein:

(i) the beta chain CDR3 of the anti-gp100 TCR comprises the amino acid sequence as set forth in SEQ ID NO: 10;

(ii) the beta chain CDR2 of the anti-gp100 TCR comprises the amino acid sequence as set forth in SEQ ID NO: 9;

(iii) the beta chain CDR1 of the anti-gp100 TCR comprises the amino acid sequence as set forth in SEQ ID NO: 6;

(iv) the alpha chain CDR3 of the anti-gp100 TCR comprises the amino acid sequence as set forth in SEQ ID NO: 7;

(v) the alpha chain CDR2 of the anti-gp100 TCR comprises the amino acid sequence as set forth in SEQ ID NO: 8; and (vi) the alpha chain CDR1 of the anti-gp100 TCR comprises the amino acid sequence as set forth in SEQ ID NO: 5.

2. The nucleic acid molecule of claim 1, wherein the anti-gp100 TCR binds to an epitope of gp100 consisting of an amino acid sequence as set forth in SEQ ID NO: 13.

3. The nucleic acid molecule of claim 2, wherein the epitope is complexed with an HLA class I molecule selected from an HLA-A, HLA-B, HLA-C, HLA-E, HLA-F, and HLA-G allele.

4. The nucleic acid molecule of claim 3, wherein the HLA class I molecule is an HLA-A*24 allele, optionally selected from an HLA-A*24:01 allele, an HLA-A*24:02 allele, and an HLA-A*24:03 allele.

5. The nucleic acid molecule of claim 1, wherein (i) the alpha chain variable domain of the anti-gp100 TCR comprises the amino acid sequence of a variable domain present in the amino acid sequence set forth SEQ ID NO: 1;

(ii) the beta chain variable domain of the anti-gp100 TCR comprises the amino acid sequence of a variable domain present in the amino acid sequence set forth SEQ ID NO: 2; or (iii) both (i) and (ii).

6. The nucleic acid molecule of claim 1, wherein:

(a) the alpha chain of the anti-gp100 TCR further comprises a constant region, wherein the constant region is different from endogenous constant region of the alpha chain, and wherein (i) the alpha chain constant region comprises an amino acid sequence having at least about 85% sequence identity to a constant region present in the amino acid sequence set forth SEQ ID NO: 1; or (ii) the alpha chain constant region comprises an amino acid sequence comprising at least 1 amino acid substitution relative to a constant region present in the amino acid sequence set forth SEQ ID NO: 1;

(b) the beta chain of the anti-gp100 TCR further comprises a constant region, wherein the constant region is different from endogenous constant regions of the beta chain, and wherein (i) the beta chain constant region comprises an amino acid sequence having at least about 85% sequence identity to a constant region present in the amino acid sequence set forth SEQ ID NO: 2; or (ii) the beta chain constant region comprises an amino acid sequence comprising at least 1 amino acid substitutions relative to a constant region present in the amino acid sequence set forth SEQ ID NO: 2; or (c) both (a) and (b).

7. The nucleic acid molecule of claim 1, wherein (i) the alpha chain of the anti-gp100 TCR comprises the amino acid sequence set forth in SEQ ID NO: 1;

(ii) the beta chain of the anti-gp100 TCR comprises the amino acid sequence set forth in SEQ ID NO: 2; or (iii) both (i) and (ii).

8. The nucleic acid molecule of claim 1, wherein the second nucleotide sequence (i) is one or more siRNAs that reduce the expression of endogenous TCRs, wherein the one or more siRNAs are complementary to a target sequence within a nucleotide sequence encoding a constant region of the endogenous TCRs;

(ii) encodes Cas9; or (iii) both (i) and (ii).

9. The nucleic acid molecule of claim 1, wherein the anti-gp100 TCR comprises an alpha chain constant region, a beta chain constant region, or both; and wherein the alpha chain constant region, the beta chain constant region, or both comprises an amino acid sequence having at least 1 substitution within the target sequence relative to the corresponding amino acid sequence of an endogenous TCR.

10. A vector comprising the nucleic acid molecule of claim 1.

11. A T cell receptor (TCR) or an antigen binding portion thereof comprising the alpha chain variable domain and the beta chain variable domain of the anti-gp100 TCR of claim 1.

12. A bispecific TCR comprising a first antigen-binding domain and a second antigen-binding domain, wherein the first antigen-binding domain comprises the TCR or an antigen-binding portion thereof of claim 11.

13. A cell comprising the nucleic acid molecule of claim 1.

14. A method of treating a cancer in a subject in need thereof, comprising administering to the subject the cell of claim 13.

15. A method of engineering an antigen-targeting cell, comprising transducing a cell collected from a subject in need of a T cell therapy with the nucleic acid molecule of claim 1.

* * * * *

SEQUENCE LISTING

```
<160> NUMBER OF SEQ ID NOS: 56

<210> SEQ ID NO 1
<211> LENGTH: 273
<212> TYPE: PRT
<213> ORGANISM: Artificial Sequence
<220> FEATURE:
<223> OTHER INFORMATION: alpha chain amino acid sequence

<400> SEQUENCE: 1

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Ala
                100                 105                 110

Thr Asp Ser Trp Gly Lys Leu Gln Phe Gly Ala Gly Thr Gln Val Val
            115                 120                 125

Val Thr Pro Asp Ile Gln Asn Pro Asp Pro Ala Val Tyr Gln Leu Arg
        130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
        210                 215                 220

Ser Cys Asp Val Lys Leu Val Glu Lys Ser Phe Glu Thr Asp Thr Asn
```

-continued

```
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
                260                 265                 270

Glx

<210> SEQ ID NO 2
<211> LENGTH: 324
<212> TYPE: PRT
<213> ORGANISM: Artificial Sequence
<220> FEATURE:
<223> OTHER INFORMATION: beta chain amino acid sequence

<400> SEQUENCE: 2

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
                100                 105                 110

Gly Asp Ser Ala Leu Tyr Phe Cys Ala Ser Ser Leu Leu Pro Glu Gly
            115                 120                 125

Thr Gly Arg Val Ser Gly Tyr Thr Phe Gly Ser Gly Thr Arg Leu Thr
            130                 135                 140

Val Val Glu Asp Leu Asn Lys Val Phe Pro Pro Glu Val Ala Val Phe
145                 150                 155                 160

Glu Pro Ser Glu Ala Glu Ile Ser His Thr Gln Lys Ala Thr Leu Val
                165                 170                 175

Cys Leu Ala Thr Gly Phe Phe Pro Asp His Val Glu Leu Ser Trp Trp
                180                 185                 190

Val Asn Gly Lys Glu Val His Ser Gly Val Ser Thr Asp Pro Gln Pro
            195                 200                 205

Leu Lys Glu Gln Pro Ala Leu Asn Asp Ser Arg Tyr Cys Leu Ser Ser
        210                 215                 220

Arg Leu Arg Val Ser Ala Thr Phe Trp Gln Asn Pro Arg Asn His Phe
225                 230                 235                 240

Arg Cys Gln Val Gln Phe Tyr Gly Leu Ser Glu Asn Asp Glu Trp Thr
                245                 250                 255

Gln Asp Arg Ala Lys Pro Val Thr Gln Ile Val Ser Ala Glu Ala Trp
                260                 265                 270

Gly Arg Ala Asp Cys Gly Phe Thr Ser Val Ser Tyr Gln Gln Gly Val
            275                 280                 285

Leu Ser Ala Thr Ile Leu Tyr Glu Ile Leu Leu Gly Lys Ala Thr Leu
        290                 295                 300

Tyr Ala Val Leu Val Ser Ala Leu Val Leu Met Ala Met Val Lys Arg
305                 310                 315                 320
```

-continued

```
Lys Asp Phe Glx

<210> SEQ ID NO 3

<400> SEQUENCE: 3

000

<210> SEQ ID NO 4

<400> SEQUENCE: 4

000

<210> SEQ ID NO 5
<211> LENGTH: 6
<212> TYPE: PRT
<213> ORGANISM: Artificial Sequence
<220> FEATURE:
<223> OTHER INFORMATION: alpha CDR1

<400> SEQUENCE: 5

Asp Ser Ala Ile Tyr Asn
1               5

<210> SEQ ID NO 6
<211> LENGTH: 5
<212> TYPE: PRT
<213> ORGANISM: Artificial Sequence
<220> FEATURE:
<223> OTHER INFORMATION: alpha CDR2

<400> SEQUENCE: 6

Pro Arg His Asp Thr
1               5

<210> SEQ ID NO 7
<211> LENGTH: 13
<212> TYPE: PRT
<213> ORGANISM: Artificial Sequence
<220> FEATURE:
<223> OTHER INFORMATION: alpha CDR3

<400> SEQUENCE: 7

Cys Ala Val Ala Thr Asp Ser Trp Gly Lys Leu Gln Phe
1               5                   10

<210> SEQ ID NO 8
<211> LENGTH: 7
<212> TYPE: PRT
<213> ORGANISM: Artificial Sequence
<220> FEATURE:
<223> OTHER INFORMATION: beta CDR1

<400> SEQUENCE: 8

Ile Gln Ser Ser Gln Arg Glu
1               5

<210> SEQ ID NO 9
<211> LENGTH: 6
<212> TYPE: PRT
<213> ORGANISM: Artificial Sequence
<220> FEATURE:
<223> OTHER INFORMATION: beta CDR2

<400> SEQUENCE: 9
```

-continued

```
Phe Tyr Glu Lys Met Gln
1               5

<210> SEQ ID NO 10
<211> LENGTH: 18
<212> TYPE: PRT
<213> ORGANISM: Artificial Sequence
<220> FEATURE:
<223> OTHER INFORMATION: beta CDR3

<400> SEQUENCE: 10

Cys Ala Ser Ser Leu Leu Pro Glu Gly Thr Gly Arg Val Ser Gly Tyr
1               5                   10                  15

Thr Phe

<210> SEQ ID NO 11

<400> SEQUENCE: 11

000

<210> SEQ ID NO 12

<400> SEQUENCE: 12

000

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 13

Val Tyr Phe Phe Leu Pro Asp His Leu
1               5

<210> SEQ ID NO 14

<400> SEQUENCE: 14

000

<210> SEQ ID NO 15

<400> SEQUENCE: 15

000

<210> SEQ ID NO 16
<211> LENGTH: 119
<212> TYPE: PRT
<213> ORGANISM: Artificial Sequence
<220> FEATURE:
<223> OTHER INFORMATION: B2m amino acid sequence

<400> SEQUENCE: 16

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
```

```
        50                55                60
Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

<210> SEQ ID NO 17
<211> LENGTH: 819
<212> TYPE: DNA
<213> ORGANISM: Artificial Sequence
<220> FEATURE:
<223> OTHER INFORMATION: alpha chain nucleotide sequence

<400> SEQUENCE: 17

```
atggagaccc tcttgggcct gcttatcctt tggctgcagc tgcaatgggt gagcagcaaa        60
caggaggtga cgcagattcc tgcagctctg agtgtcccag aaggagaaaa cttggttctc       120
aactgcagtt tcactgatag cgctatttac aacctccagt ggtttaggca ggaccctggg       180
aaaggtctca catctctgtt gcttattcag tcaagtcaga gagagcaaac aagtggaaga       240
cttaatgcct cgctggataa atcatcagga cgtagtactt atacattgc agcttctcag        300 cctggtgact cagccaccta cctctgtgct gtcgcaactg acagctgggg gaaattgcag       360
tttggagcag ggacccaggt tgtggtcacc ccagatatcc agaaccctga ccctgccgtg       420
taccagctga gagactctaa atccagtgac aagtctgtct gcctattcac cgattttgat       480
tctcaaacaa atgtgtcaca aagtaaggat tctgatgtgt atatcacaga caaaactgtg       540
ctagacatga ggtctatgga cttcaagagc aacagtgctg tggcctggag caacaaatct       600
gactttgcat gtcaaacgc cttcaacaac agcattattc agaagacac cttcttcccc         660 agcccagaaa gttcctgtga tgtcaagctg gtcgagaaaa gctttgaaac agatacgaac       720
ctaaactttc aaaacctgtc agtgattggg ttccgaatcc tcctcctgaa agtggccggg       780
tttaatctgc tcatgacgct gcggctgtgg tccagctga                              819
```

<210> SEQ ID NO 18
<211> LENGTH: 972
<212> TYPE: DNA
<213> ORGANISM: Artificial Sequence
<220> FEATURE:
<223> OTHER INFORMATION: beta chain nucleotide sequence

<400> SEQUENCE: 18

```
atgcttagtc ctgacctgcc tgactctgcc tggaacacca ggctcctctg ccatgtcatg        60
ctttgtctcc tgggagcagt ttcagtggct gctggagtca tccagtcccc aagacatctg       120
atcaaagaaa gagggaaac agccactctg aaatgctatc ctatccctag acacgacact         180
gtctactggt accagcaggg tccaggtcag gacccccagt tcctcatttc gttttatgaa       240
aagatgcaga gcgataaagg aagcatccct gatcgattct cagctcaaca gttcagtgac       300
tatcattctg aactgaacat gagctccttg gagctggggg actcagccct gtacttctgt       360
gccagcagcc tcctaccgga agggacaggc cgtgtaagtg ctacacctt cggttcgggg        420 accaggttaa ccgttgtaga ggacctgaac aaggtgttcc cacccgaggt cgctgtgttt       480
gagccatcag aagcagagat ctcccacacc caaaaggcca cactggtgtg cctggccaca       540
```

-continued

```
ggcttcttcc ctgaccacgt ggagctgagc tggtgggtga atgggaagga ggtgcacagt      600
ggggtcagca cggacccgca gcccctcaag gagcagcccg ccctcaatga ctccagatac      660
tgcctgagca gccgcctgag ggtctcggcc accttctggc agaaccccg caaccacttc       720 cgctgtcaag tccagttcta cgggctctcg gagaatgacg agtggaccca ggatagggcc      780
aaacccgtca cccagatcgt cagcgccgag gcctggggta gagcagactg tggctttacc      840
tcggtgtcct accagcaagg ggtcctgtct gccaccatcc tctatgagat cctgctaggg      900
aaggccaccc tgtatgctgt gctggtcagc gcccttgtgt tgatggccat ggtcaagaga      960
aaggatttct ga                                                           972
```

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

-continued

```
<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000
```

-continued

```
<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
```

-continued

```
<400> SEQUENCE: 50

000

<210> SEQ ID NO 51

<400> SEQUENCE: 51

000

<210> SEQ ID NO 52
<211> LENGTH: 661
<212> TYPE: PRT
<213> ORGANISM: Artificial Sequence
<220> FEATURE:
<223> OTHER INFORMATION: gp100 Amino Acid Sequenc

<400> SEQUENCE: 52

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
                20                  25                  30

Leu Gly Val Ser Arg Gln Leu Arg Thr Lys Ala Trp Asn Arg Gln Leu
            35                  40                  45

Tyr Pro Glu Trp Thr Glu Ala Gln Arg Leu Asp Cys Trp Arg Gly Gly
        50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
        130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
            195                 200                 205

Ile Thr Asp Gln Val Pro Phe Ser Val Ser Val Ser Gln Leu Arg Ala
        210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
            275                 280                 285

Gln Val Val Leu Gln Ala Ala Ile Pro Leu Thr Ser Cys Gly Ser Ser
        290                 295                 300

Pro Val Pro Gly Thr Thr Asp Gly His Arg Pro Thr Ala Glu Ala Pro
```

-continued

```
305              310              315              320

Asn Thr Thr Ala Gly Gln Val Pro Thr Thr Glu Val Val Gly Thr Thr
                325              330              335

Pro Gly Gln Ala Pro Thr Ala Glu Pro Ser Gly Thr Thr Ser Val Gln
                340              345              350

Val Pro Thr Thr Glu Val Ile Ser Thr Ala Pro Val Gln Met Pro Thr
                355              360              365

Ala Glu Ser Thr Gly Met Thr Pro Glu Lys Val Pro Val Ser Glu Val
    370              375              380

Met Gly Thr Thr Leu Ala Glu Met Ser Thr Pro Glu Ala Thr Gly Met
385              390              395              400

Thr Pro Ala Glu Val Ser Ile Val Val Leu Ser Gly Thr Thr Ala Ala
                405              410              415

Gln Val Thr Thr Thr Glu Trp Val Glu Thr Thr Ala Arg Glu Leu Pro
                420              425              430

Ile Pro Glu Pro Glu Gly Pro Asp Ala Ser Ser Ile Met Ser Thr Glu
                435              440              445

Ser Ile Thr Gly Ser Leu Gly Pro Leu Leu Asp Gly Thr Ala Thr Leu
    450              455              460

Arg Leu Val Lys Arg Gln Val Pro Leu Asp Cys Val Leu Tyr Arg Tyr
465              470              475              480

Gly Ser Phe Ser Val Thr Leu Asp Ile Val Gln Gly Ile Glu Ser Ala
                485              490              495

Glu Ile Leu Gln Ala Val Pro Ser Gly Glu Gly Asp Ala Phe Glu Leu
                500              505              510

Thr Val Ser Cys Gln Gly Gly Leu Pro Lys Glu Ala Cys Met Glu Ile
                515              520              525

Ser Ser Pro Gly Cys Gln Pro Pro Ala Gln Arg Leu Cys Gln Pro Val
    530              535              540

Leu Pro Ser Pro Ala Cys Gln Leu Val Leu His Gln Ile Leu Lys Gly
545              550              555              560

Gly Ser Gly Thr Tyr Cys Leu Asn Val Ser Leu Ala Asp Thr Asn Ser
                565              570              575

Leu Ala Val Val Ser Thr Gln Leu Ile Met Pro Gly Gln Glu Ala Gly
                580              585              590

Leu Gly Gln Val Pro Leu Ile Val Gly Ile Leu Leu Val Leu Met Ala
                595              600              605

Val Val Leu Ala Ser Leu Ile Tyr Arg Arg Arg Leu Met Lys Gln Asp
    610              615              620

Phe Ser Val Pro Gln Leu Pro His Ser Ser Ser His Trp Leu Arg Leu
625              630              635              640

Pro Arg Ile Phe Cys Ser Cys Pro Ile Gly Glu Asn Ser Pro Leu Leu
                645              650              655

Ser Gly Gln Gln Val
            660

<210> SEQ ID NO 53
<211> LENGTH: 21
<212> TYPE: DNA
<213> ORGANISM: Artificial Sequence
<220> FEATURE:
<223> OTHER INFORMATION: siRNA-TCRa-1

<400> SEQUENCE: 53
guaaggauuc ugauguguat t                                              21
```

```
<210> SEQ ID NO 54
<211> LENGTH: 21
<212> TYPE: DNA
<213> ORGANISM: Artificial Sequence
<220> FEATURE:
<223> OTHER INFORMATION: siRNA-TCRa-2

<400> SEQUENCE: 54
uacacaucag aauccuuact t                                              21

<210> SEQ ID NO 55
<211> LENGTH: 21
<212> TYPE: DNA
<213> ORGANISM: Artificial Sequence
<220> FEATURE:
<223> OTHER INFORMATION: siRNA-TCRb-1

<400> SEQUENCE: 55
ccaccauccu cuaugagaut t                                              21

<210> SEQ ID NO 56
<211> LENGTH: 21
<212> TYPE: DNA
<213> ORGANISM: Artificial Sequence
<220> FEATURE:
<223> OTHER INFORMATION: siRNA-TCRb-2

<400> SEQUENCE: 56
aucucauaga ggaugguggt t                                              21
```